United States Patent [19]

Brazhnikov et al.

[11] 4,145,917

[45] Mar. 27, 1979

[54] METHOD OF MEASURING PROPERTIES OF A FLUID IN A CONTAINER AND DEVICE FOR REALIZING SAME

[75] Inventors: Nikolai I. Brazhnikov; Nikolai N. Khavsky; Vladimir F. Kravchenko, all of Moscow, U.S.S.R.

[73] Assignee: Vsesojuzny Nauchno-Issledovatelsky I Konstruktorsky Institut "Tsvetmetavtomatika", Moscow, U.S.S.R.

[21] Appl. No.: 787,327

[22] Filed: Apr. 14, 1977

[51] Int. Cl.² .......................................... G01N 29/02
[52] U.S. Cl. ...................................................... 73/53
[58] Field of Search .......... 73/32 R, 53, 61 R, 61.1 R, 73/67.5 R, 67.1, 290 V

[56] References Cited

U.S. PATENT DOCUMENTS

| 2,932,818 | 4/1960 | Lubkin | 73/67.8 R X |
| 3,050,720 | 8/1962 | Rich | 73/290 V X |

FOREIGN PATENT DOCUMENTS 1300172 6/1962 France ................................. 73/290 V

*Primary Examiner*—Charles A. Ruehl
*Attorney, Agent, or Firm*—Lackenbach, Lilling & Siegel

[57] ABSTRACT

A method of measuring properties of a fluid in a container, wherein acoustic oscillation pulses are periodically applied to said fluid through the container wall and normally thereto, is disclosed. The acoustic signals are received in the zone of application of the acoustic oscillation pulses as envelopes of the pulse acoustic reverberation produced between the outer surface of the container wall and the fluid, said envelopes being used to form an electrical signal carrying information on the properties of the fluid. A device for measuring properties of a fluid in a container comprises an acoustic transducer positioned directly on the outer surface of the container wall and a series-connected circuit, composed of an electric pulse time delay unit, a gating pulse generator and a gating acoustic signal amplifier, coupled to the acoustic transducer. The device also comprises a pulse acoustic reverberation envelope detector having an input connected to the output of the gating amplifier and an output electrically connected to the input of a data-carrying electric signal shaper which is electrically coupled to a measuring unit.

22 Claims, 49 Drawing Figures

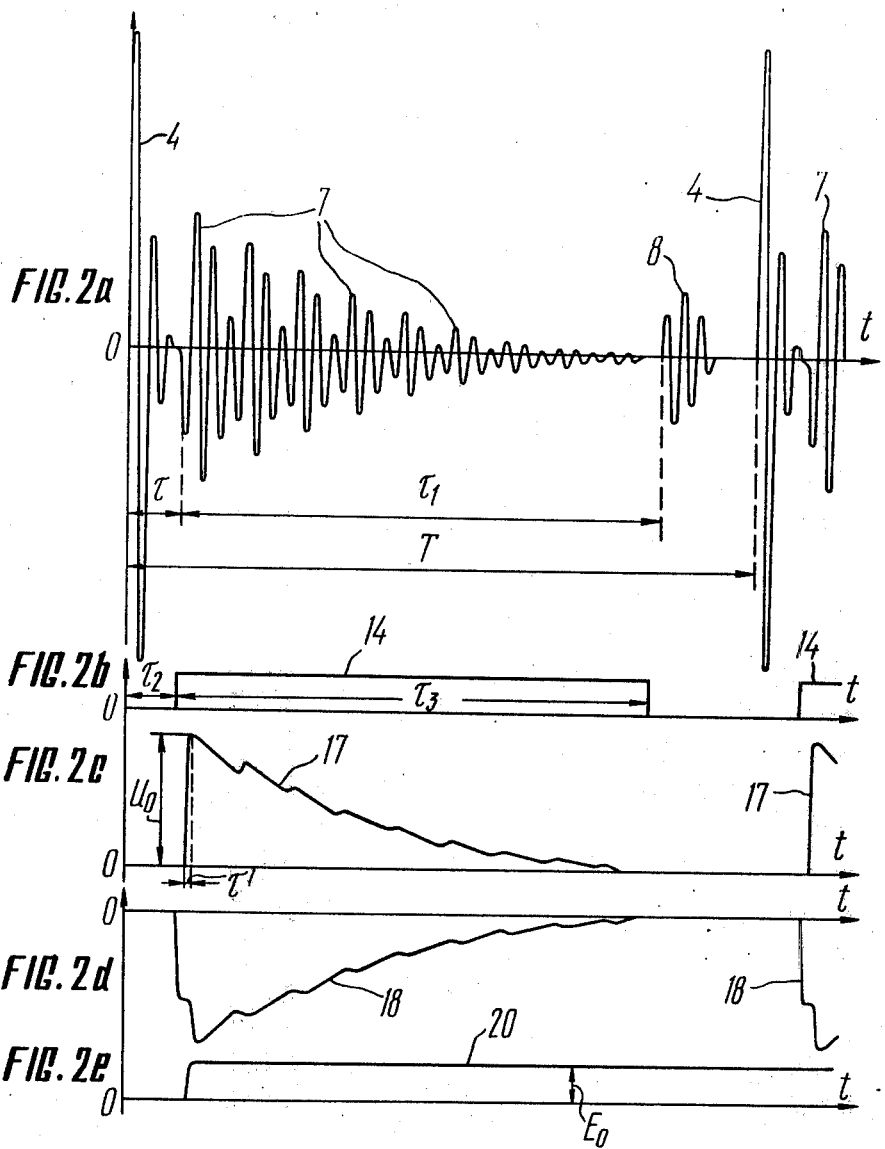

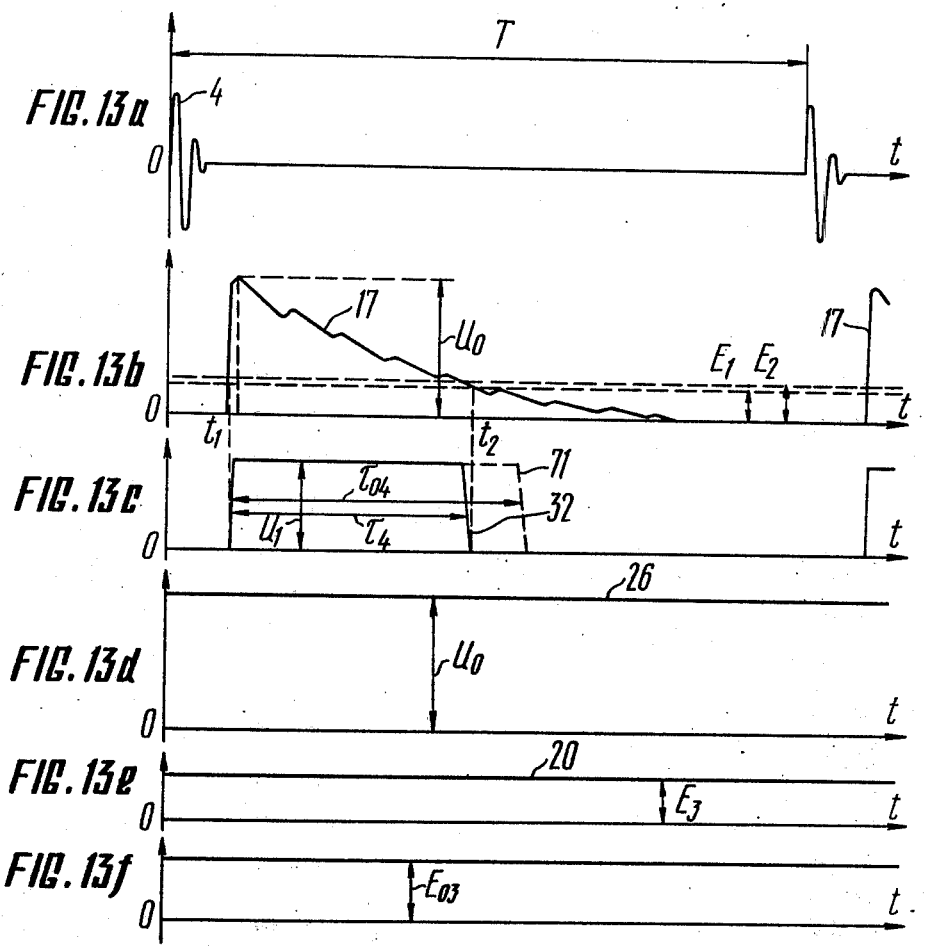

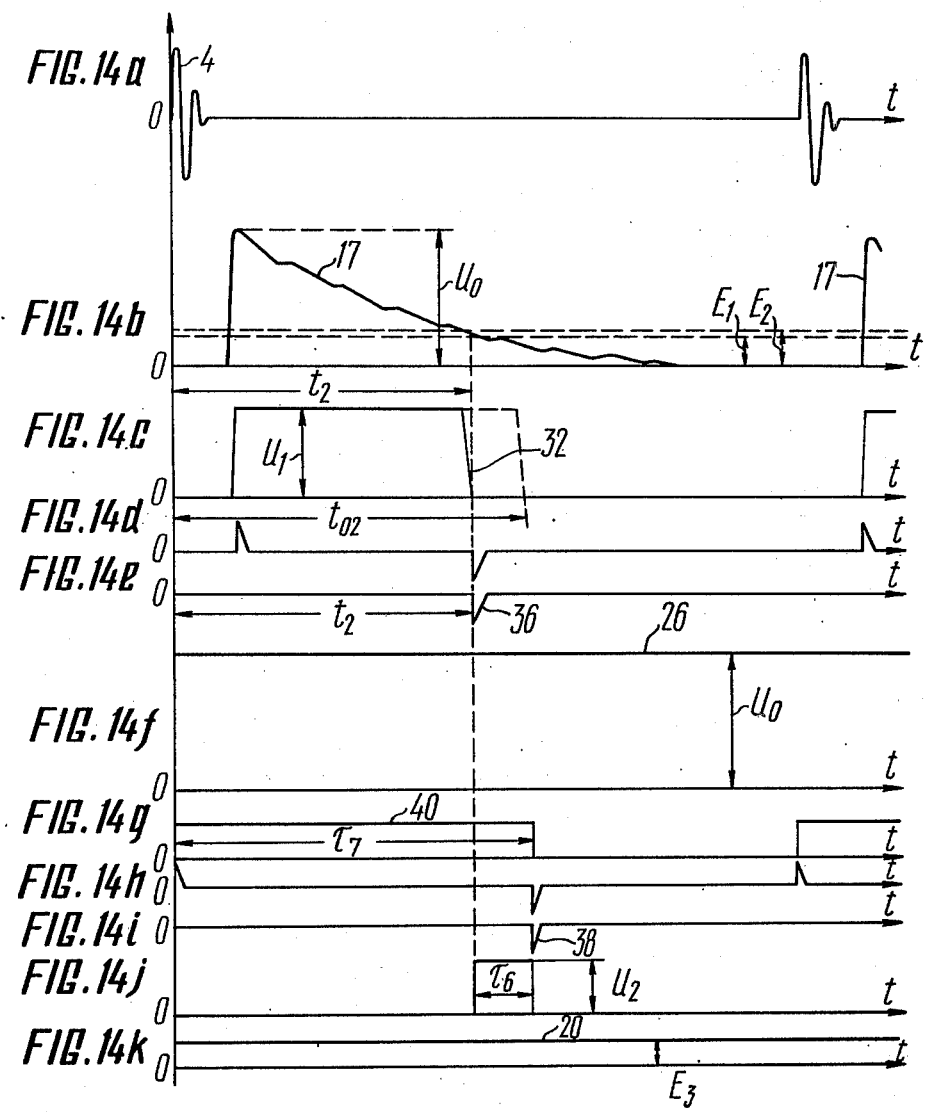

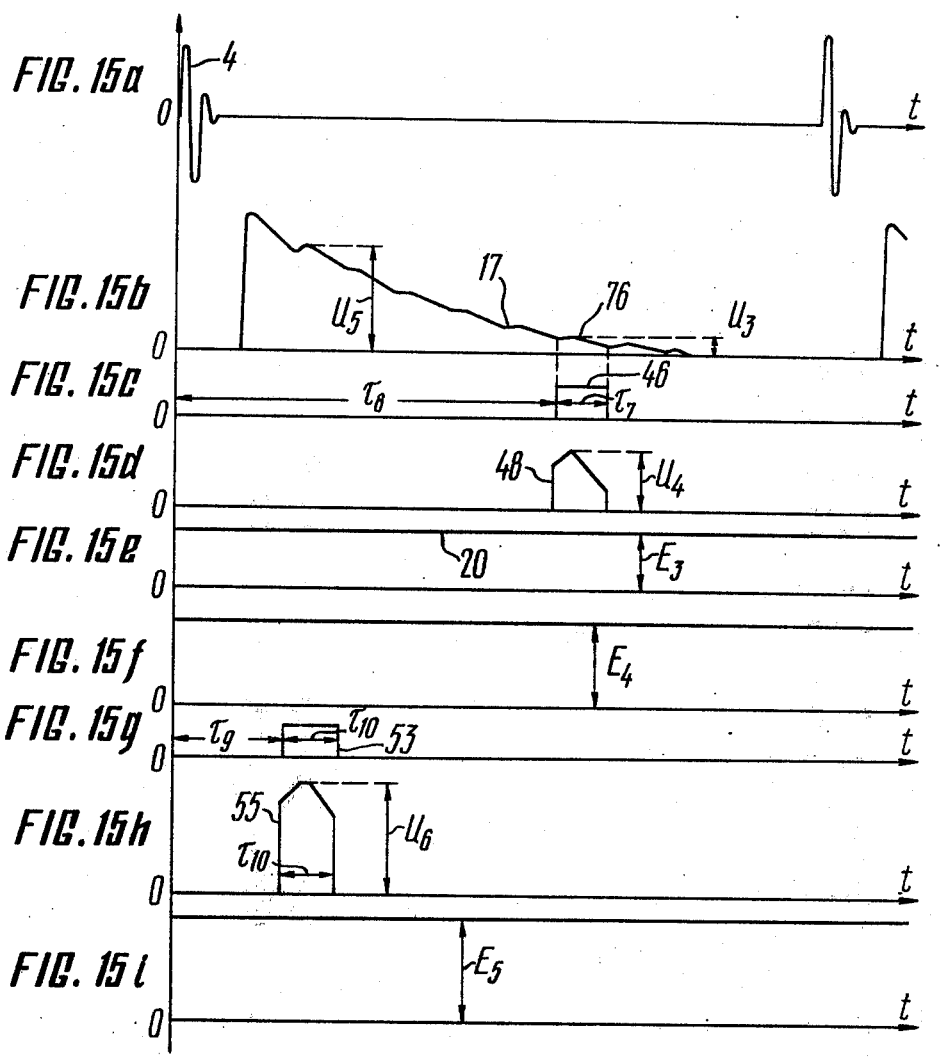

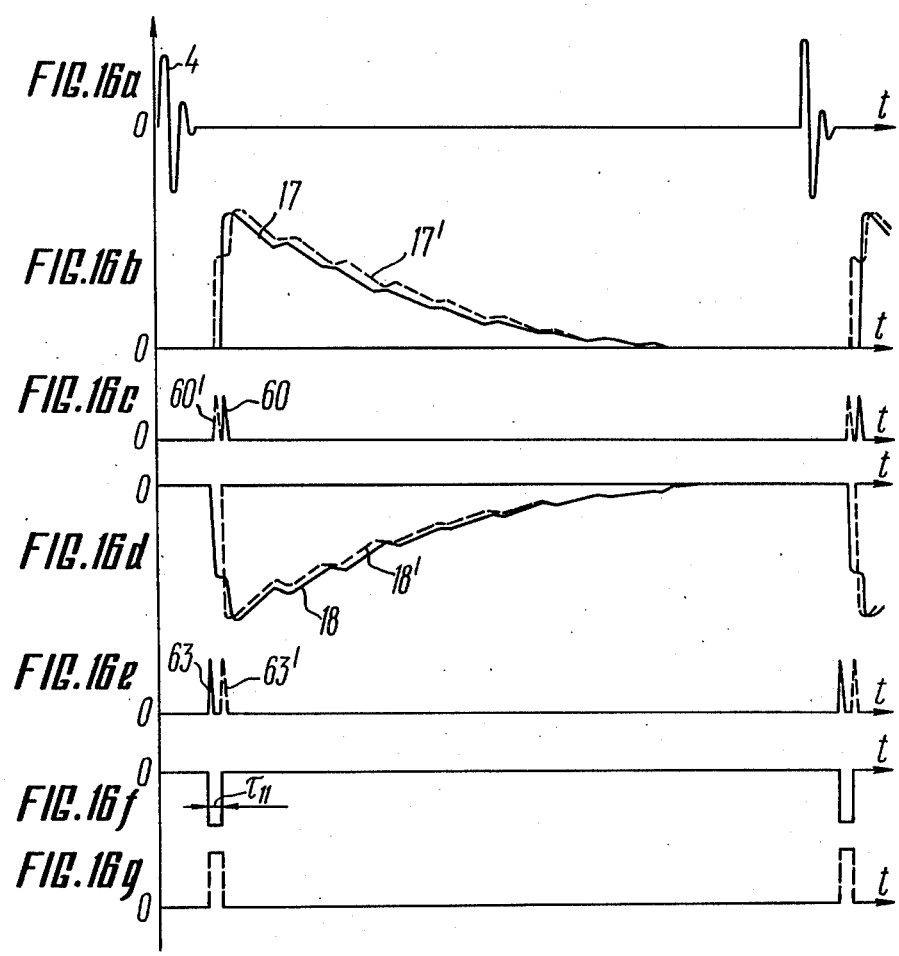

METHOD OF MEASURING PROPERTIES OF A FLUID IN A CONTAINER AND DEVICE FOR REALIZING SAME

FIELD OF THE INVENTION

The present invention relates to equipment for automatic control of technological parameters in production processes of various branches of industry by means of acoustic oscillations and, in particular, to a method of measuring properties of a fluid in a container and a device for realizing this method.

The invention can be employed in automatic control systems in hydrometallurgic and concentration processes in ferrous and non-ferrous metallurgy, chemical, petroleum and food industries and other fields for automatic non-contact measuring of properties of a fluid placed in a container.

Controlled production processes can be characterized by various factors destablilizing properties of media and producing various obstacles and difficulties for means employed to measure the properties of such media. Among such factors in a number of industrial production processes are unstable or increased attenuation of acoustic oscillations in the substance of interest, unstable permittivity, stirring of the fluid by air bubbles, unstable concentration of suspended solid particles in the fluid and others.

The basic requirement set for methods and devices for measuring properties of a fluid in a container, e.g. concentration of liquid solutions, consists of minimizing the effect of the forementioned destabilizing factors on the reliability and accuracy of measurements. Among other requirements are sensitivity of measurements, safety of servicing personnel, simplicity of the design of the device and low commercial prices.

DESCRIPTION OF THE PRIOR ART

In order to measure properties of a fluid in a container methods of various physical natures and different devices realizing such methods can be used. They can be divided into two groups, depending on their technological principles: probe and non-contact methods. In the first group sensitive probes supplying the information on the fluid are introduced into the container holding this fluid and are in contact with said fluid. In the second group sensitive elements are outside the container and are not subjected to the direct effects of the fluid whose properties are to be measured.

There is known in the first group a resonance method and a device for measuring properties of a substance. This method consists of an ultrasonic source being placed in the container, as well as a reflector which is positioned at a fixed distance therefrom. A stationary ultrasonic wave is formed between the source and the reflector. The frequency of this wave depends on the properties of the medium, in which the ultrasonic source and reflector are located. The device realizing this method comprises, apart from the ultrasonic source and the reflector, a wide-band electric generator electrically connected to the ultrasonic source and a recorder which registers variations of the frequency of acoustic self-excitement of the fluid layer between the ultrasonic source and reflector.

However, this method and device are characterized by poor reliability and accuracy in measuring properties of viscous media comprisng suspended solid particles owing to the sticking of these particles to the ultrasonic source and reflector.

There are known in the first group a capacity method and a device for measuring properties of a fluid.

This method consists of a sensitive element being placed inside a container and made as two plates (or rods) with a clearance therebetween, the capacity of the sensitive element, which depends on the capacitivity of the medium in this clearance, beng measured and the capacity serving as an indication of the required property of the fluid in the container. The device for realization of this method comprises, apart from the capacitive sensitive element, a recorder of variations in the capacity of this element, which accompany variations in the properties of the fluid.

The above described method and device for measuring properties of a fluid are deficient in that they are not reliable owing to instability of capacitivity of the media and variations of the clearance of the sensitive element and, consequently, its capacity due to suspended particles in the fluid.

There are known also among the first group an impedance method and a device for measuring properties of a fluid.

This method consists of measuring electrical impedance of an ultrasonic source placed inside the container, which changes depending on the properties of the fluid in which the source is locat3ed. The device realizing this method comprises the ultrasonic source coupled to an electric oscillation generator and a recorder to register variations of the source impedance.

The above described method and device are characterized by poor accuracy of measuring properties of the fluid and insufficient reliability of measuring. This is due to minor variations of the source electric impedance caused by changes in acoustic damping of the source by the fluid, when its properties vary.

The general drawback of all three above described methods and devices of the first group is that the sensitive elements are to be placed inside the container, which requires an interruption in the technological process for installation, preventive maintenance and repair of the device. Besides, the service life and reliability of such devices drops sharply, when containers are filled with agressive media.

These drawbacks are not present in methods and devices of the above mentioned second group.

There are known among the second group a radioisotope method and a device for measuring properties of fluids, e.g. concentration of liquid solutions.

This method consists of measuring the variations in absorption of a radioactive radiation passing through the technological container in the direction crossing its axis in response to changes of properties of the fluid in the container. The device for realization of this method comprises a radioactive radiation source, a receiver placed on both sides of the container on its external surface and a recorder coupled to the receiver.

This method and device for detection of media boundaries are deficient in that they are not accurate, complicated in design and expensive, as well as a potential radiation hazard for servicing personnel.

There is known a method of detecting liquid presence in a container.

This method consists of acoustic oscillation pulses being formed and periodically applied to the fluid through the wall of the container, in which it is contained, normally to said wall, acoustic signals being received after they pass through the wall of the container and an electric signal being shaped, which carries information on the properties of the fluid in question.

In the above described method the amplitude of the electric signal is the indication of the properties of the fluid in question. Variations of this amplitude are dependent upon the differences in passing of the acoustic wave inside the container through the fluid in this container, which properties are measured by said method.

There is known a device for measuring properties of a fluid in a container comprising an acoustic transducer coupled to a pulse generator and located directly on the external surface of the container wall. This transducer produces acoustic oscillation pulses supplied to the fluid through the container wall and then received and converted into acoustic signals fed to the signal input of a shaper of a data-carrying electrical signal carrying information on the properties of the fluid in question. The output of the shaper is electrically coupled to the input of a measuring unit connected to a recorder of the electric signal amplitude which is the indication of the variations in the properties of the fluid.

This method for measuring properties of a fluid in a container and the device realizing this method do not permit, when employed in various branches of industry, e.g. in mining, hydrometallurgy and some chemical industries, an adequate level of accuracy, which results in significant errors, as well as more complicated construction and, consequently, a higher commerical price of the device.

This can be accounted for by the fact that the cross-sections of the containers are large, sometimes 8-10 meters, which leads to sharp diffraction divergence of the acoustic wave and considerable reduction of its amplitude in the zone of reception. In order to reduce the diffraction effect the radiation source and the frequency of radiated wave should be increased, which requires a sharp rise in the power of the electric oscillations generator involving, respectively, more complicated equipment and higher prices of the device.

Besides, gas bubbles and solid particles present in the liquid media inside the container result in significant divergence of the acoustic wave propagating therein, characterized by the exponential attenuation of the amplitude of the received wave with the increase of the container size. This is the source of many errors and in a number of cases makes this method and device practically unusable.

SUMMARY OF THE INVENTION

An object of this invention is to provide a method of measuring properties of a fluid in a container and a device to realize this method in order to ensure high reliability of the fluid property measurement.

Another object of this invention is to increase the accuracy of such measurements.

Yet another object of the present invention is to make the design of the device and its operation simplier and, consequently, reduce its commercial price and servicing expenditures.

These objects are achieved by a method for measuring properties of a fluid in a container, consisting of acoustic oscillation pulses being formed and periodically applied to the fluid through the wall of the container, in which it is contained, and normally to said wall, acoustic signals which have passed through the container wall being received and an electric signal being formed thereof, which carries information on properties of the fluid. According to the invention, heteropolar envelopes of pulse acoustic reverberation produced between the outer surface of the container wall and the fluid in question are used as acoustic signals and said envelopes are received in the zone of application of the acoustic oscillation pulses.

It is advisable that the electric signal carrying information on properties of the fluid be formed by means of determination of the area limited by one of the envelopes of pulse acoustic reverberation and its zero level and finding the ratio of said area to the time interval proportional to the interval between the two successively applied acoustic oscillation pulses.

It is useful that the maximum amplitude of said envelope be additionally measured and compared to the ratio of the area limited by said envelope and its zero level to the time interval proportional to the time interval between two successively applied acoustic oscillation pulses.

It is preferable that the electric signal carrying information on properties of the fluid in question be formed by means of separation of portions on the leading and trailing edges of one envelope of pulse acoustic reverberation, which respective ends are located on two amplitude levels at least one order of magnitude less than the maximum amplitude of said envelope, and determination of the time interval between said portions.

It is advantageous that the lower of said two amplitude levels be variable in proportion to changes of the maximum amplitude of said envelope of pulse acoustic reverberation.

It is preferable that the electric signal carrying information on properties of the fluid in question be formed be means of separation of a portion of the trailing edge of one of the envelopes of pulse acoustic reverberation, whose ends are located on two amplitude levels at least one order of magnitude less than the maximum amplitude of said envelope, formation of an electric pulse corresponding to the separated portion, shaping a reference electric pulse at the instant corresponding to one of the positions of the formed electric pulse within the operating measuring range and measuring the time interval between these pulses.

It is preferable that said reference pulse be formed with a time delay proportional to the variations of the maximum amplitude of said envelope.

It is good practice that the electric signal carrying information on properties of the fluid in question be formed by means of separating a portion of the trailing edge of one of the envelopes of pulse acoustic reverberation, which length is approximately equal to double the time required for the acoustic oscillation pulse to pass through the container wall and which is spaced from the leading edge of said envelope a distance divisible at least by double the time required for the acoustic oscillation pulse to pass through the container wall and determination of the maximum amplitude of the envelope in this portion.

It is preferable that an additional portion of said envelope be separated between its main portion and the leading edge, which is spaced from the main portion of said envelope a distance divisible by double the time required for the acoustic oscillation pulse to pass through the container wall, and maximum amplitudes of the envelope be compared on said main and additional portions.

It is also useful that the electric signal carrying information on properties of the fluid in question be formed by means of determination of the sign of the time interval between the leading edges of two heteropolar envelopes of pulse acoustic reverberation.

The above described objects are achieved by a device for measuring properties of a fluid in a container comprising an acoustic transducer coupled to a pulse generator and placed directly on the outer surface of the container wall in order to produce acoustic oscillation pulses applied to the fluid through the container wall and later received and converted into acoustic signals which are fed to the signal input of a shaper of a data-carrying electric signal carrying information on properties of the fluid in question. An output of the shaper is electrically connected to the input of a measuring unit coupled to a recorder. According to the invention, there is provided a series-connected circuit comprising an electric pulse time delay unit having an input connected to the output of the pulse generator, a gating pulse generator and an acoustic signal selective amplifier having a signal input coupled to the acoustic transducer. This ensures reception and conversion of the acoustic signals by means of said acoustic transducer. There is also provided a detector, of the envelope of pulse acoustic reverberation produced between the outer surface of the container wall and the fluid, having an input coupled to the output of the gating amplifier and an output electrically connected to the signal input of the data-carrying electric signal shaper and ensures the use of said envelope of pulse acoustic reverberation as the acoustic signal.

It is advantageous that the data-carrying electric signal shaper to be made of an integrator of the pulse acoustic reverberation envelope.

It is useful that the device be provided with a peak detector of the pulse acoustic reverberation envelope having an input coupled to the output of the pulse acoustic reverberation envelope detector having an output electrically connected to a second input of the measuring unit, this measuring unit being built of a differential circuit.

It is also possible that the device be provided with a peak detector of the pulse acoustic reverberation envelope having an input coupled to the output of said pulse acoustic reverberation envelope detector, an electric signal dividing unit having inputs connected to the outputs of said peak detector of the pulse acoustic reverberation envelope and the integrator of the pulse acoustic reverberation envelope, and an output connected to said input of the measuring unit, and a reference electric signal shaper having an output coupled to the second input of the measuring unit, the measuring unit being built of a differential circuit.

It is preferable that the device be provided with a unit for limiting the pulse acoustic reverberation envelope on two amplitude levels, which produces an electric pulse of which the leading and trailing edges correspond to two portions of the pulse acoustic reverberation envelope, the ends thereof being located on two amplitude levels. An input of said limiting unit is coupled to the output of said detector of the pulse acoustic reverberation envelope and an output is coupled to the input of the data-carrying electric signal shaper, an electric pulse duration measuring unit being used as said data-carrying electric signal shaper.

It is also useful that the device be provided with a peak detector of the pulse acoustic reverberation envelope, which is intended for adjusting the lower amplitude level of said separated portions of the pulse acoustic reverberation envelope. The input of the peak detector is in this case coupled to the output of said detector of the pulse acoustic reverberation envelope and the output is electrically connected to the controlled input of the unit for limiting the pulse acoustic reverberation envelope at two amplitude levels.

It is also preferable that the device be provided with a data-carrying electric signal shaper comprising a series-connected circuit composed of the unit for limiting the pulse acoustic reverberation envelope on two amplitude levels, which is designed to separate a portion on the trailing edge of the pulse acoustic reverberation envelope, and a differentiating unit designed to produce an electric pulse corresponding to said separated portion on the trailing edge of the envelope. The input of the data-carrying electric signal shaper is the input of the limiting unit and the output is the output of the differentiating unit. There is provided an electric pulse time delay unit designed to produce a reference electric pulse, having an input coupled to the output of said pulse generator and an output coupled to the second input of the measuring unit, the measuring unit being a time interval measuring unit.

It is also advantageous that the device be provided with a peak detector of the pulse acoustic reverberation envelope having its input coupled to the output of said detector of the pulse acoustic reverberation envelope, and an electric pulse time delay control unit having an input electrically connected to the output of the peak detector and an output connected to the input of the electric pulse time delay unit.

It is advisable that the device be provided with a data-carrying electric signal shaper comprising a series-connected circuit composed of a second electric pulse time delay unit, a second gating pulse generator, a gating amplifier of the amplitude of the pulse acoustic reverberation envelope, which is designed to separate a portion on the trailing edge of said envelope, and a peak detector of the separated portion of the pulse acoustic reverberation envelope. The input of the peak detector is coupled to the output of the gating amplifier. The input of the second electric pulse time delay unit is connected to the output of the pulse generator and serves as the controlled input of the data-carrying electric signal shaper. The signal input of the shaper is the signal input of the gating amplifier of the amplitude of the pulse acoustic reverberation envelope and the output of the shaper is the output of the peak detector.

In addition, it is useful that the device be provided with a series-connected circuit comprising a third electric pulse time delay unit, a third generator of gating pulses, a second gating amplifier of the amplitude of the pulse acoustic reverberation envelope, which is designed to separate an additional portion on the trailing edge of said envelope, which is located between said main portion of the envelope and its leading edge, and a second peak detector of the separated additional portion of the pulse acoustic reverberation envelope. The input of the third unit for electric pulse time delay is coupled to the output of the pulse generator, the signal input of the second gating amplifier is coupled to the output of the detector of the pulse acoustic reverberation envelope and the output of the second peak detector is electrically coupled to the second input of the measuring unit, the measuring unit itself being built about a differential circuit.

It is also possible that the device be provided with a series-connected circuit comprising a third electric pulse time delay unit, a third gating pulse generator, a second gating amplifier of the amplitude of the pulse acoustic reverberation envelope, which is designed to separate an additional portion on the trailing edge of said envelope, which is located between said main portion of the envelope and its leading edge, and a second peak detector of the separated additional portion of the pulse acoustic reverberation envelope. The input of the third electric pulse time delay unit being coupled to the output of the pulse generator and the signal input of the second gating amplifier is coupled to the output of the detector of the pulse acoustic reverberation envelope. There are provided an electric signal dividing unit having inputs electrically connected to the outputs of the first and second peak detectors of said separated portions of the pulse acoustic reverberation envelope and an output coupled to said input of the measuring unit, and a reference electric signal shaper having an output connected to the second input of the measuring unit, the measuring unit itself being built of a differential circuit.

It is advisable that in the device a standard electric pulse shaping unit be used as the data-carrying electric signal shaper in order to produce a standard electric pulse corresponding to the leading edge of the pulse acoustic reverberation envelope and the device be provided with a series-connected circuit comprising a detector of the second pulse acoustic reverberation envelope having an input coupled to the output of said acoustic signal gating amplifier, and a second standard electric pulse shaping unit, in order to produce a standard electric pulse corresponding to the leading edge of the second envelope of pulse acoustic reverberation, having an output coupled to the second input of the measuring unit, the measuring unit itself being made as a unit for measuring the time difference between formation of standard electric pulses corresponding to the leading edges of both heteropolar envelopes of pulse acoustic reverberation.

The above described method of measuring properties of a fluid in a container and a device realizing this method possess a number of advantages over the known methods and devices.

The above described method and device permit a significant reduction of errors in measuring properties of a fluid in a container and, consequently, improve accuracy and reliability of measurements.

Firstly, the method completely eliminates errors in measurements of properties of a fluid in a container caused by diffraction divergence of the acoustic wave in fluids whose properties are measured in a container, since here no need arises to register the wave propagating in said fluid. The diffraction effect of acoustic oscillations propagating in the wall and registered in accordance with the present invention is much less pronounced and has no practical influence upon the measurement accuracy.

Secondly, the above described method permits complete elimination of errors caused by substantial attenuation of the acoustic wave propagating in fluids whose properties are measured. This is achieved by the present method by the envelope of pulse acoustic reverberation produced between the outer surface of the container wall and the fluid in question being taken as the acoustic signals indicative of the fluid property of interest and the parameters of this envelope are independent of the divergence of the acoustic wave in fluids, e.g. liquid solutions, filled in the container.

Besides, the device realizing the above described method, according to the invention, is constructionally much simplier owing to the use of a smaller acoustic transducer, a much less powerful electric oscillation generator and reception of acoustic oscillations by the same acoustic transducer. This is ensured by the fact that there is no need for a sharp increase of the acoustic wave power, as in the case of the known device, wherein the acoustic wave has to pass through large industrial containers. This is also due to the fact that the acoustic signals are received by the same acoustic transducer which produces pulses of acoustic oscillations and at the same zone where the acoustic oscillation pulses are applied to the wall of the container holding the fluid of interest.

BRIEF DESCRIPTION OF THE DRAWINGS

Other objects and advantages of the present method of measuring properties of a fluid in a container and a device for realization of this method will become more apparent from the following description of preferred embodiments thereof, taken in conjunction with the accompanying drawings, wherein:

FIG. 2a–2e are graphs showing time and amplitude, plotted on the abscissa and on the ordinate, respectively, of an electric oscillation pulse of a pulse generator, gating pulses, envelopes of pulse acoustic reverberation and a data-carrying electric signal, respectively;

FIGS. 13a–13f are graphs showing time and amplitude, on the abscissa and on the ordinate, respectively, of an electric oscillation pulse of a generator, a pulse acoustic reverberation envelope with two amplitude limiting levels, a bidirectionally clipped pulse, the output signal of the peak detector of said envelope, data-carrying and recorded signals, respectively;

FIGS. 14a–14k are graphs of the electric oscillation pulse of the generator, the pulse acoustic reverberation envelope with two amplitude limiting levels, the bidirectionally clipped pulse, pointed voltage pulses shaped in the differentiating unit, the output pulse of the differentiating unit, the output signal of the peak detector, a pulse of a specified duration, pointed voltage pulses shaped in the differentiating unit, the reference electric pulse, the data-carrying pulse and electric signal, respectively;

FIGS. 15a–15i are graphs of the electric oscillation pulse of the generator, the pulse acoustic reverberation envelope, the first gating pulse, a pulse corresponding to the first separated portion of the trailing edge of said envelope, the data-carrying electric signal at the output of the peak detector, a reference electric signal having an amplitude proportional to the maximum envelope amplitude, a second gating pulse, a pulse corresponding to the second separated portion of the envelope trailing edge, direct current voltage obtained at the output of the peak detector, respectively; and FIGS. 16a–16g are graphs of the generator electric oscillation pulse, the first pulse acoustic reverberation envelope and the respective standard electric pulse, the second pulse acoustic reverberation envelope and the respective standard electric pulse, rectangular pulses whose duration is dependent upon the time difference between shaping of the standard pulses, respectively.

DETAILED DESCRIPTION OF THE INVENTION

Figure 1:
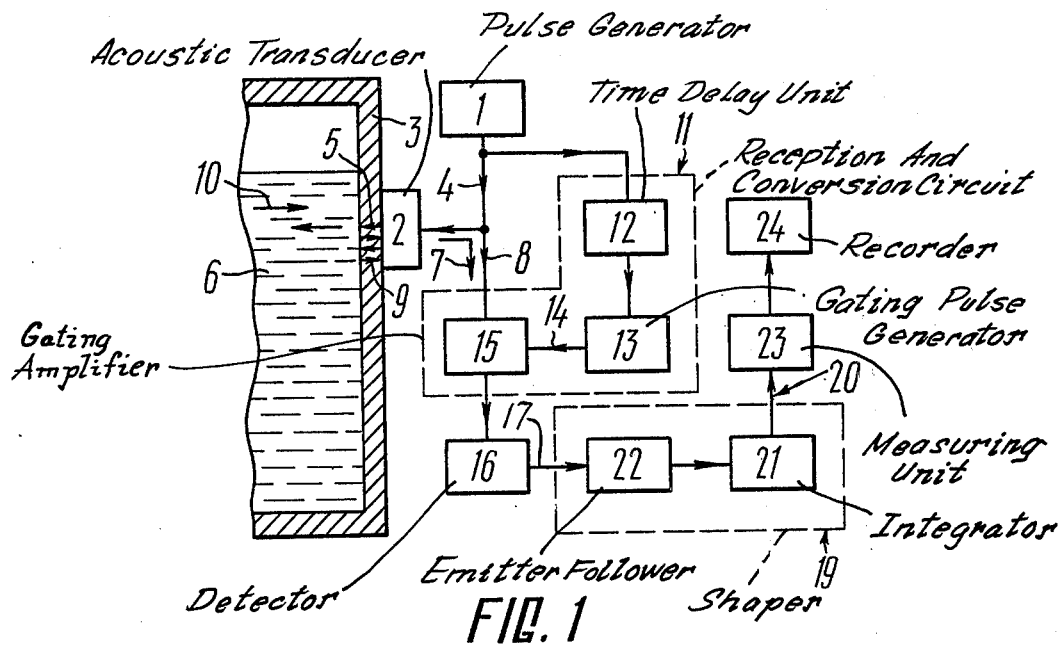
FIG. 1 is a block diagram showing the proposed device for measuring properties of a fluid in a container, according to the invention.

The proposed device for measuring properties of a fluid in a container comprises a pulse generator 1 (FIG. 1) and an acoustic transducer 2 coupled to the pulse generator and positioned directly on an outer surface of a wall 3 of the container.

In the disclosed embodiment of the device a piezoelectric transducer (cf., for example, U.S. Pat. No. 2,931,233) is used as the acoustic transducer and the pulse generator 1 is built of a circuit of an impact excitation pulse generator (cf., for example, Brazhnikov N. I. "Ultrasonic Methods", Moscow, Energia Publ., 1965, pp. 146–149).

In response to electric oscillation pulses 4 of the generator 1, the acoustic transducer 2 produces acoustic oscillation pulses 5 which are applied to a fluid 6 through the container wall 3 and are later received and transduced into acoustic signals 7 and 8.

For better understanding of the method of measuring properties of a fluid in a container, time charts are shown in FIGS. 2a–2e.

The signal 7 (FIG. 2a), the amplitude of the electric oscillation pulse 4 being plotted as the ordinate) is conditioned by multiple reflected acoustic oscillation pulses 9 (FIG. 1) which are the cause of pulse acoustic reverberation between the outer surface of the container wall 3 and the monitored fluid 6. The signal 8 is conditioned by the acoustic oscillation pulse 10 reflected from the opposite side of the inner surface of the container wall 3 and passing two times through the fluid 6. Said signals 7 and 8 are separated in time from the beginning of application of the acoustic oscillation pulse 5 to the wall 3 by the values $\tau$ and $\tau + \tau_1$, respectively.

The device features a circuit 11 (FIG. 1) intended in general cases for reception and conversion of the acoustic signals 7 carrying information on the fluid 6. The circuit 11 consists of a unit 12 for time delay of electric pulses for a time $\tau_2 \leq \tau$ (FIG. 2b) having an input coupled to the output of the pulse generator 1 (FIG. 1), a generator 13 of gating pulses 14 with a duration $\tau_3 \leq \tau + \tau_1 - \tau_2$ (FIG. 2b, wherein the amplitude of the pulse 14 is plotted along the ordinate) and a gating amplifier 15 (FIG. 1) of acoustic signals, having a signal input coupled to the acoustic transducer 2. All of the above enumerated units being connected in series. Such circuit 11 ensures separation of the acoustic signals 7 from the acoustic signal 8 and the pulses 4 of the generator 1.

In this embodiment the gating pulse generator is built of a circuit of a rectangular pulse generator and the gating amplifier is made according to the known circuit (cf., for example, Brazhnikov N. I, "Ultrasonic Phasemetering" Moscow, Energia Publ., 1968, pp. 163–164, FIGS. 4–5).

The device also comprises a detector 16 of one of the envelopes 17 or 18 (FIGS. 2c and 2d), wherein amplitudes of these envelopes 17 and 18 are respectively plotted along the ordinates) of pulse acoustic reverberation having an input coupled to the output of the gating amplifier 15 and an output coupled to the signal input of a shaper 19 of a data-carrying electric signal 20. The detector 16 permits the use of said envelopes 17 or 18 as the acoustic signals.

For convenience only one of the envelopes, the envelope 17 of pulse acoustic reverberation, is used hereinafter in the text of the description. In the described embodiment of the device the envelope detector is built of a diode circuit of a demodulator (cf., for example, Brazhnikov, "Ultrasonic Phasemetering", Moscow, Energia Publ., 1968, p. 179, FIGS. 4–10).

The electric signal carrying information on properties of the fluid of interest can be shaped in different ways.

One of the methods consists of determining the area which is bounded by one of the envelopes 17 of pulse acoustic reverberation and its zero level. Then it is necessary to determine the ratio of this area to the time interval proportional to the time interval T (FIG. 2a) between two successively applied acoustic oscillation pulses 5 (FIG. 1). In this case the shaper 19 of the data-carrying electric signal 20 (FIG. 2e, wherein the amplitude of the signal 20 is plotted along the ordinate) is built of an integrator 21 (FIG. 1) of the pulse acoustic reverberation envelope 17 having an input electrically connected to the output of the detector 16 of said envelope 17 by means of an emitter follower 22 and an output connected to the input of a measuring unit 23 coupled to a recorder 24.

In the embodiment being described the integrator 21 is made according to the known resistor-capacitor circuit (cf., for example, French Pat. No. 2,087,703 FIG. 1).

A digital counter, a register or a relay is used as the recorder 24, depending on what type of information on the fluid of interest is required. The embodiment being described uses the known recorder (cf., for example, U.S. Pat. No. 3,345,861) and the measuring unit is built of a circuit converting the data-carrying signal into a direct current voltage of a higher amplitude.

In order to reduce errors in measuring properties of the fluid, which are caused by the unstable amplitude of the acoustic oscillation pulse 5 applied to the container wall 3, the maximum amplitude $U_o$ (FIG. 2c) of the envelope 17 of pulse acoustic reverberation is additionally measured and compared to the ratio of the area limited by said envelope 17 and its zero level to the time interval proportional to the time interval T (FIG. 2a) between two successively applied acoustic oscillation pulses 5 (FIG. 1). For this purpose the device is provided with a peak detector 25 (FIG. 3) of the pulse acoustic reverberation envelope 17, which produces an electric signal 26 equal in voltage to the maximum amplitude $U_o$ of this envelope 17. In this embodiment the peak detector 25 is built of the known diode-capacitor circuit (cf., for example, Brazhnikov N. I., "Ultrasonic Phasemetering", Moscow, Energia Publ., 1968, pp. 17-19, FIGS. 2.4).

The input of said peak detector 25 is coupled to the output of the detector 16 of the pulse acoustic reverberation envelope 17 and the output is electrically connected to the second input of the measuring unit 23 by means of an emitter follower 27 featuring an adjustable output in order to shape a reference electric signal 28, the measuring unit 23 being built of a differential circuit.

The device ensures elimination of the zero drift of the recorder 24, which is caused by the above mentioned unstable amplitude of the acoustic oscillation pulse 5 applied to the wall 3.

Figure 3:
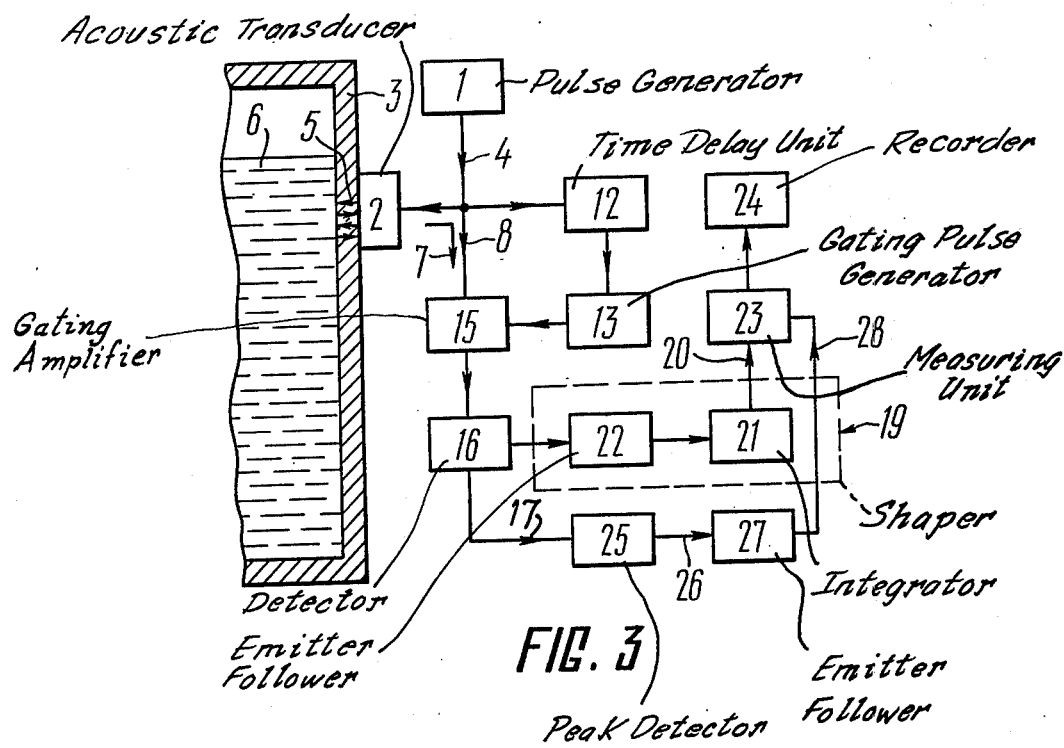
FIG. 3 is a block diagram showing the device of FIG. 1, provided with a detector of the pulse acoustic reverberation envelope in the electrical circuit of the proposed device, according to the invention.

Another embodiment of the device, analogous to the embodiment of FIG. 3, can be used to achieve lesser sensitivity variations in measurements of the fluid property, caused by said instability of the amplitude of the pulse 5.

The only difference consists in that, in addition to said peak detector 25 of the pulse acoustic reverberation enveloper 17, which has its input coupled to the output of the detector 16 of the pulse acoustic reverberation 17, there is provided an electric signal dividing unit 29 (FIG. 4) having inputs coupled to the outputs of said peak detector 25 of the pulse acoustic reverberation envelope 17 and the integrator 21 of the pulse acoustic reverberation envelope 17 and an output coupled to the first input of the measuring unit 23. The device also comprises a reference electric signal shaper 30 having an output coupled to the second input of the measuring unit 23, the measuring unit 23 being built of a differential circuit.

In this embodiment of the device the electric signal dividing unit 29 is built of the known synch-follow-up circuit (cf., for example, Brazhnikov N. I., "Ultrasonic Methods", Energia Publ., Moscow, 1965, pp. 223-224, FIGS. 5. 11).

The electric signal carrying information on the properties of the fluid of interest can also be shaped by separating portions on the leading and trailing edges of one of the envelopes 17 of pulse acoustic reverberation, which respective ends lie on two amplitude levels at least one order of magnitude less than the maximum amplitude of said envelope 17, and finding the time interval $\tau_4$ between said portions.

This is achieved by an embodiment of the device, which is analogous to the embodiment of FIG. 1.

The only difference consists of the device comprising a unit 31 (FIG. 5) for limiting the pulse acoustic reverberation envelope 17 on two amplitude levels, which shapes an electric pulse 32 with a duration $\tau_4$ and an amplitude $U_1$, of which the leading and trailing edges correspond to two portions of the pulse acoustic reverberation envelope 17, their ends being located on said two amplitude levels. The leading and trailing edges of the pulse 32 correspond to instants $t_1$ and $t_2$. In this embodiment the unit 31 for limiting the pulse acoustic reverberation envelope is built of the known diode circuit (cf., for example, Goldenberg L. M., "Theory and Calculation of Pulse Devices in Semiconductor Instruments", Moscow, Sviaz Publ., 1969, pp. 170-171, FIG. 3.7).

In this case the input of the limiting unit 31 is coupled to the output of the detector 16 of the pulse acoustic reverberation envelope 17 and the output is coupled to the input of the shaper 19 of the data-carrying electric signal 20.

Figure 5:
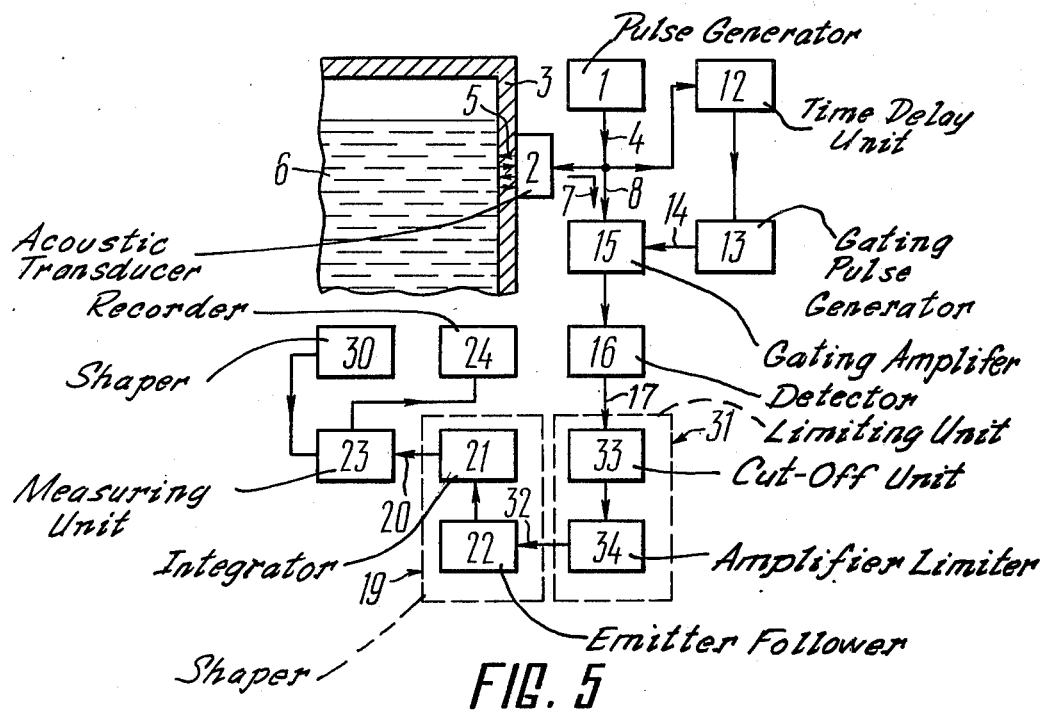
FIG. 5 is a block diagram showing the device of FIG. 1, provided with a unit for limiting the envelope of pulse acoustic reverberation on two amplitude levels, a data-carrying electric signal shaper and a reference electric signal shaper in the electrical circuit of the proposed device, according to the invention.
Figure 6:
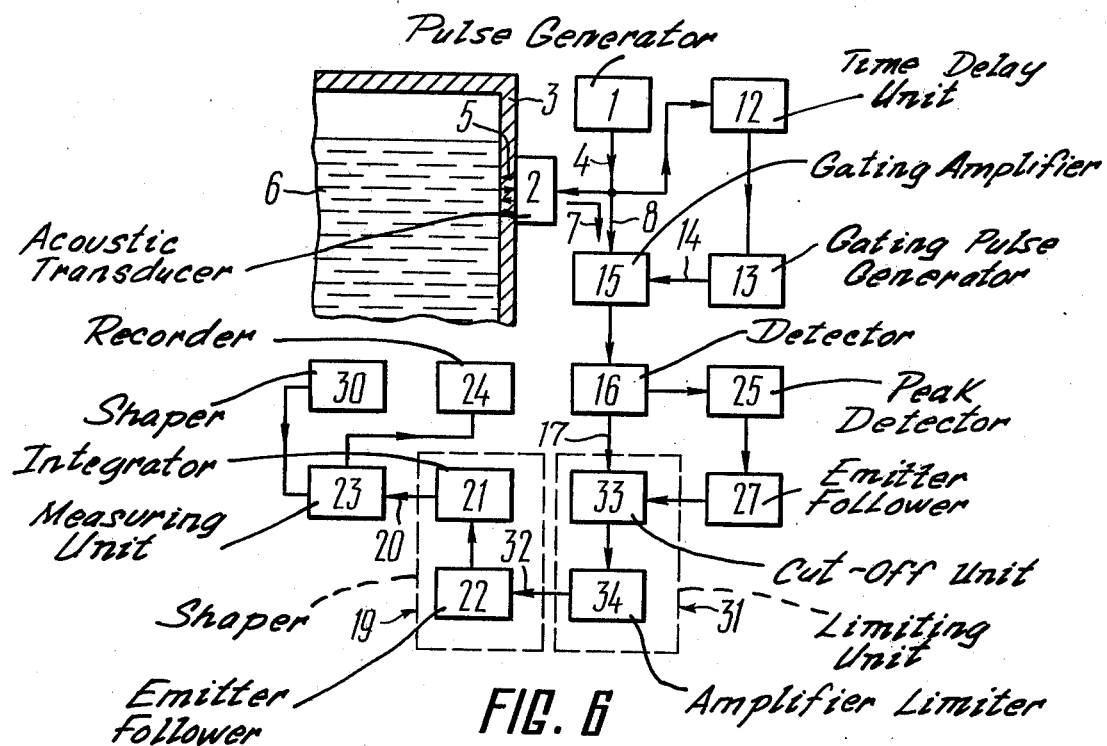
FIG. 6 is a block diagram showing the device of FIG. 5, featuring a peak detector of the pulse acoustic reverberation envelope in order to control the lower amplitude level in said unit for limiting the pulse acoustic reverberation envelope, according to the invention.

The unit 31 in this embodiment is made of the following series-connected known units: a unit 33 for envelope cut-off at the lower amplitude level and an amplifier-limiter 34 for the upper amplitude level of said envelope 17. Said shaper 19 of the data-carrying electric signal is an electric pulse duration measuring unit which is made, as shown in FIG. 5, as the series-connected emitter follower 22 and the integrator 21, the output thereof being the output of the shaper 19 of the data-carrying electric signal 20.

In order to register the deviations of the measured property of the fluid from its initial value, the data-carrying electric signal is compared in the measuring unit 23, built of a differential circuit, to the reference electrical signal of the shaper 30. This reference electric signal has an amplitude equal to the amplitude of the data-carrying signal 20, the duration thereof corresponding to the duration $\tau_{04}$ of the pulse 32 as in the initial value of the fluid property being measured.

In order to reduce the effect of the unstable amplitude of the acoustic oscillation pulses 5 applied to the container wall 3 upon the accuracy of measurement of properties of the fluid, the lower of the two amplitude limitation levels of the envelope 17 is set variable in proportion to the variations of the maximum amplitude of said envelope. This is achieved by the device being additionally provided with a peak detector 25 (FIG. 6) of the pulse acoustic reverberation envelope 17, which is designed to adjust the lower amplitude level of said separated portions of the pulse acoustic reverberation envelope 17. In this case the input of the peak detector 25 is coupled to the output of the detector 16 of the pulse acoustic reverberation envelope 17 and the output is electrically connected by means of the emitter follower 27 to the controlled input of the unit 32 for limiting the pulse acoustic reverberation envelope 17 at two amplitude levels.

The electric signal carrying information on properties of the fluid may also be produced by means of separating a portion on the trailing edge of one of the envelopes 17, of which the ends are located on two amplitude levels at least one order of magnitude less than the maximum amplitude of said envelope, shaping an electric pulse corresponding to the separated portion, shaping a reference electric pulse at an instant of time corresponding to one of the positions of the produced electric pulse within the operating measurement range and measuring the time interval between said pulses.

This is achieved by means of an embodiment of the device analogous to that of FIG. 1.

The only difference consists in that the shaper 19 of the data-carrying electric signal comprises several series-connected units: a unit 31 (FIG. 7) for limiting the pulse acoustic reverberation envelope 17 on two amplitude levels, which is intended for separation of a portion on the trailing edge of the pulse acoustic reverberation envelope 17, and a differentiating unit 35 intended for shaping an electric pulse 36 corresponding to said separated portion on the trailing edge of the envelope 17 and spaced from the moment of application of the acoustic oscillation pulse 5 to the container wall 3 by the time interval $t_2$. In this case the input of the shaper 19 of the data-carrying electric signal 36 is the input of the limiting unit 31, and the output is the output of the differentiating unit 35. The device in this case is also provided with a unit 37 for the time delay of electric pulses for a time $\tau_5$, which is intended for shaping a reference electric pulse 38. The input of the time delay unit 37 is coupled to the output of the pulse generator 1 and the output is coupled to the second input of the measuring unit 23. In this case the measuring unit 23 is a unit for measuring time intervals $\tau_6 = \tau_5 - \tau_2$, built in this embodiment of the device of a flip-flop (cf., for example, Brazhnikov N. I., "Ultrasonic Methods", Moscow, Energia Publ., 1965, pp. 166-167, FIG. 3.14). The time delay unit 37 is built of a shaper 39 of pulses 40 of specified duration, which is set equal to the required time delay $\tau_5$, and a second differentiating unit 41 connected in series thereto and intended for shaping the reference electric pulse 38 corresponding to the trailing edge of the pulse 40.

The effect of the amplitude instability of the acoustic oscillation pulses 5 applied to the container wall 3 upon the accuracy of measurement of the fluid properties can be reduced by shaping the reference pulse 38 with a time delay proportional to the variations of the maximum amplitude $U_o$ of said envelope 17.

For this purpose the device additionally comprises a peak detector 25 (FIG. 8) of the pulse acoustic reverberation envelope 17 having an input coupled to the output of said detector 16 of the pulse acoustic reverberation envelope 17 and an electric pulse time delay control unit 42 having an input electrically connected to the output of the peak detector 25 by means of the emitter follower 27 and an output connected to the controlled input of the electric pulse time delay unit 37. Such input is the controlled input of the shaper 39, when said shaper 39 of pulses 40 of a specified duration is used in the time delay unit 37.

The electric signal carrying information on the properties of the fluid can also be shaped by means of separating a portion on the trailing edge of one of the pulse acoustic reverberation envelopes 17, which has a length $\tau_7$ approximately equal to the value $\tau$ of the time required for the acoustic oscillation pulse 5 to pass twice through the container wall 3 and spaced from the leading edge of said envelope 17 a distance divisible by the time $\tau$ required for the acoustic oscillation pulse 5 to pass twice through the container wall 3, and determining the maximum amplitude of the envelope 17 at this portion.

For this purpose, there is proposed an embodiment of the device, which is analogous to that of FIG. 1.

The only difference consists of the shaper 19 of the data-carrying electric signal 20 comprising a circuit 43 (FIG. 9) composed of the following series-connected units: a second unit 44 for electric pulse time delay, a second generator 45 of gating pulses 46 and a gating amplitude amplifier 47 of the pulse acoustic reverberation envelope 17. This circuit 43 is designed to separate a portion on the trailing edge of said envelope 17 as a separate pulse 48. The shaper 19 also comprises a peak detector 49 of the separated portion of the pulse acoustic reverberation envelope 17 having an input coupled to the output of the gating amplifier 47. In this case the input of the second electric pulse time delay unit 44 is coupled to the output of the pulse generator 1 and serves as the controlled input of the shaper 19 of the data-carrying electric signal 20, the signal input being the signal input of the gating amplitude amplifier 47 of the envelope 17 of pulse acoustic reverberation. The output of the shaper 19 is the output of the peak detector 49.

The effect of the instability of the amplitude of the acoustic oscillation pulses 5 applied to the container wall 3 upon the accuracy of measurements of the properties of the fluid can be reduced here by an additional portion of said envelope 17 being separated between its main portion and the leading edge, which is spaced from the main portion of this envelope 17 a value divisible by $\tau$ equal to the time required for the acoustic oscillation pulse to pass twice through the container wall 3, and the maximum amplitudes of the envelope 17 being compared on this main and additional portions.

Figure 9:
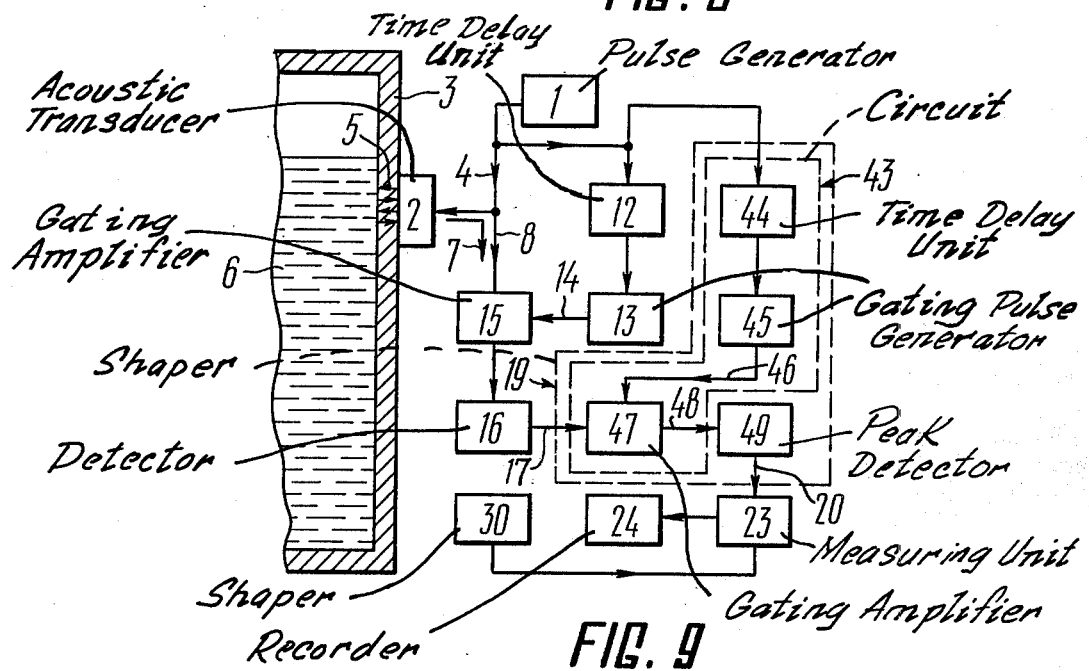
FIG. 9 is a block diagram showing the device of FIG. 1, featuring an electronic channel for separation of a portion on the trailing edge of the pulse acoustic reverberation envelope and a peak detector of said portion in the data-carrying signal shaper of the electrical circuit of the proposed device, according to the invention.

An embodiment of the device, wherein in accordance with said operations the zero drift of the recorder 24 is eliminated irrespective of the amplitude instability of the pulses 5 applied to the container wall 3, is analogous to that of FIG. 9.

The difference consists in that there is provided a circuit 50 (FIG. 10) composed of the following series-connected units: a third electric pulse time delay unit 51, and a third generator 52 of gating pulses 53, a second gating amplifier 54 of the amplitude of the pulse acoustic reverberation envelope 17, which is intended for separation of an additional portion on the trailing edge of said envelope 17 corresponding to a pulse 55. The additional portion is located between said main portion of the envelope 17 and the leading edge thereof. The circuit 50 also comprises a second peak detector 56 of the separated additional portion of the pulse acoustic reverberation envelope 17. In this case the input of the third electric pulse time delay unit 51 is coupled to the output of the pulse generator 1, the signal input of the second gating amplifier 54 is coupled to the output of the detector 16 of the pulse acoustic reverberation envelope 17, and the output of the second peak detector 56 is electrically connected to the second input of the measuring unit 23 by means of an emitter follower 57 featuring an adjustable output. Here the measuring unit 23 is built of a differentiating circuit.

An embodiment of the device, wherein not only the zero drift of the recorder 24 is eliminated but variations in the sensitivity of the fluid property measurements, caused by the above mentioned instability of the acoustic oscillation pulses 5 applied to the container wall 3, are done away with, is provided, part from the units of the device of FIG. 9. The circuit 50 (FIG. 11) is composed of the following series-connected units: a third electric pulse time delay unit 51, a third generator 52 of gating pulses 53, a second gating amplitude amplifier 54 of the pulse acoustic reverberation envelope 17, which is intended for separation of an additional portion on the trailing edge of said envelope 17 located between said main portion of the envelope 17 and the leading edge thereof, and a second peak detector 56 of the separated additional portion of the pulse acoustic reverberation envelope 17. In this case the input of the third unit 51 for electric pulse time delay is coupled to the output of the pulse generator 1 and the signal input of the second gate amplifier 54 is coupled to the output of the detector 16 of the pulse acoustic reverberation envelope 17. This device also features an electric signal dividing unit 58 whose inputs are connected to the outputs of the first and second peak detectors 49 and 56 of said separated portions of the pulse acoustic reverberation envelope 17 and whose output is coupled to the input of the measuring unit 23; and a reference electric signal shaper 30 whose output is coupled to the second input of the measuring unit 23. In this case the measuring unit 23 is built of a differential circuit and the second peak detector 56 is connected to the dividing unit 58 through the emitter follower 57.

For several fluids whose acoustic impedance is close to or more than the acoustic impedance of the container wall 3, the electric signal carrying information on the fluid properties is produced by finding the sign of the time interval between the leading edges of two heteropolar envelopes 17 and 18 of pulse acoustic reverberation. In this case the embodiment of the device is analogous to that of the device of FIG. 1.

The only difference consists in that the shaper 19 of the data-carrying electric signal 20 is a unit 59 (FIG. 12) for shaping standard electric pulses, which ensures shaping of a standard electric pulse 60 corresponding to the leading edge of the pulse acoustic reverberation envelope 17. In this embodiment of the device the standard electric pulse shaping unit 59 is built of the known amplifier-shaper circuit featuring a resistor-capacitor circuit at the input thereof (cf., for example, Goldenberg L. M., "Theory and Calculation of Semiconductor Pulsed Devices", Moscow, Sviaz Publ., 1969, pp. 181–183, FIG. 3.16). Besides, the device features a series-connected circuit comprising a detector 61 of the second pulse acoustic reverberation envelope 18 having an input coupled to the output of the acoustic signal gating amplifier 15, and a second standard electric pulse shaping unit 62 intended for shaping a standard electric pulse 63 corresponding to the leading edge of the second envelope 18 of pulse acoustic reverberation. In this case the output of the second unit 62 for shaping standard electric pulses is coupled to the second input of the measuring unit 23 and the measuring unit 23 is a unit for measuring the time difference between shaping of the standard electric pulses 60 and 63 corresponding to the leading edges of both pulse acoustic reverberation envelopes 17 and 18.

All the above described embodiments of the device can be successfully used to measure the properties of a fluid in a container. The method of measuring properties of a fluid in a container is realized in the above described embodiments of the device as follows.

The acoustic transducer 2 (FIG. 1) generates pulses 5 of acoustic oscillations U which are periodically applied to the fluid 6 through the container wall 3, wherein the fluid is filled, normally to said wall 3.

These pulses 5 are reflected on the boundary between the inner surface of the wall 3 and the fluid 6 in the direction of the outer surface of the wall 3, from which they are also reflected. Owing to multiple reflected pulses 9 in the wall 3, pulse acoustic reverberation is produced whose total acoustic signal 7 (FIG. 2a) is received by the same transducer 2 (FIG. 1). Origination of the signal 7 is spaced from the moment of application of the acoustic oscillation pulses 5 to the container wall 3 by a time interval $\tau$ (FIG. 2a) which is defined by the expression:

$$\tau = 2d/C \qquad (1)$$

wherein
d is the thickness of the container wall 3 and
C is the velocity of the propagation of acoustic oscillations in the container wall 3.

Along with said signal 7, the acoustic transducer 2 also receives from the container wall 3 an acoustic signal 8 caused by the acoustic oscillation pulse 10 which has twice passed through the fluid 6 and was reflected from the inner container wall 3. The leading edges of said signals 7 and 8 are separated in time from one another by a value $\tau_1$ (FIG. 2a) which depends upon the crosssection D of the container and the velocity $C_1$ of the propagation of acoustic oscillations in the fluid 6:

$$\tau_1 = 2D/C_1; \qquad (2)$$

The acoustic transducer 2 (FIG. 1) produced acoustic oscillation pulses 5 in response to the electric oscillation pulses 4 generated at a pulse repetition period T (FIG. 2a) by the pulse generator 1 (FIG. 1).

These pulses 4 of the generator 1, apart from being fed to the acoustic transducer 2, are supplied along with the acoustic signals 7 and 8 to the signal input of the gating amplifier 15 whose controlled input is being fed gating pulses 14 (FIG. 2b) with a duration $\tau_3$ from the generator 13 (FIG. 1) which produces said pulses from the pulses 4 of the generator 1 with a time delay $\tau_2$ (FIG. 2b). The time delay $\tau_2$ is set to be longer than the duration of the pulse 4 of the generator 1 (FIG. 1) but shorter than or equal to the time $\tau$ required for the acoustic oscillations to pass twice through the container wall 3. The duration $\tau_3$ of the gating pulse 14 is selected so that the shaping of said pulse in the generator 13 is over before the acoustic signal 8 starts to be fed to the acoustic transducer 2. In this case the following inequality is observed:

$$\tau_3 = \tau + \tau_1 - \tau_2; \qquad (3)$$

With such operation of the circuit 11, comprising along with the gating amplifier 15 the gating pulse generator 13 and the time delay unit 12, the acoustic signals 7 are separated from the acoustic signal 8 and the pulses 4 of the generator 1.

The separated acoustic signal 7 from the output of the gating amplifier 15 is supplied to the input of the detector 16 of the pulse acoustic reverberation envelope. This detector 16 separates the envelope 17 or 18 (FIGS. 2c and 2d) of the acoustic signal 7, which are envelopes of pulse acoustic reverberation produced between the outer surface of the container wall 3 (FIG. 1) and the fluid 6 in the container. In the embodiments of the device for realizing the method of measuring properties of the fluid in a container, shown in FIGS. 1,3-11, only one of the envelopes, namely the envelope 17 (FIG. 2c), of pulse acoustic reverberation, is used.

Said envelope 17 of pulse acoustic reverberation produced in the zone of the acoustic transducer 2 between the outer surface of the container wall 3 and the fluid 6 carries information on the properties of said fluid 6.

Let us consider, by way of example, one of the fluid properties, that is the concentration q of a binary solution of fluids or a solution of a solid in a liquid. It is general knowledge (cf., for example, Brazhnikov, "Ultrasonic Methods", Energia Publ., 1965, pp. 56-73) that the velocity $C_1$ of propagation of acoustic oscillations in a liquid solution is functionally dependent upon the concentration thereof and can be generally expressed as follows $$C_1 = \phi_1(q); \qquad (4)$$

Yet, the concentration q of the solution is directly proportional to the density $\rho_1$ in most cases $$\rho_1 = \rho_{01}(1 + K_1 q); \qquad (5)$$

where $\rho_{01}$ is the density of the solvent.

Thus, the acoustic impedance $Z_1$ of a liquid solution, which is equal to $\rho_1 C_1$, is dependent upon the concentration q of this solution as follows:

$$Z_1 = \rho_{01}(1 + K_1 q) \phi(q); \qquad (6)$$

Within a range of concentrations q of many liquid solutions, which is sufficiently wide for industrial purposes, the dependence (equation 6) of the acoustic impedance $Z_1$ upon the concentration q is fairly close to linear:

$$Z_1 = Z_{01}(1 + K_2 q); \qquad (7)$$

where $Z_{01}$ is the acoustic impedance of the solvent.

The proportional dependence factor $K_2$ of the impedance $Z_1$ versus the concentration q (G/l) for some water solutions ($Z_{01} = 1.48 \times 10^5$ g cm$^{-2}$ c$^{-1}$) are given in Table 1.

Table 1

| Water Solutions of: | Aluminum Sulfate | Magnesium Sulfate | Zinc Sulfate | Potassium Sulfate |
|---|---|---|---|---|
| $K_2$ G$^{-1}$ · 1 | 0.00051 | 0.00061 | 0.00039 | 0.00037 |
| Water Solutions of: | Sodium Chloride | Potassium Hydrate | Lithium Hydrate | Sodium Hydrate |
| $K_2$ G$^{-1}$ · 1 | 0.00069 | 0.00011 | 0.00025 | 0.00017 |
| Water Solutions of: | Ammonia | Nitric Acid | Sulfuric Acid | Muriatic Acid |
| $K_2$ G$^{-1}$ · 1 | 0.00005 | 0.00007 | −0.00007 | 0.00035 |

The dependence of the maximum amplitude $U_0$ of the envelope 17 (FIG. 2c) upon the ratio of acoustic impedances $Z_1$ and $Z = \rho C$ of the liquid solution and the material of the container wall 3, respectively, is determined by the following expression:

$$U_0 = EK_3 B(1 - Z_1/Z)(1 + Z_1/Z)^{-1}, \qquad (8)$$

where:

B is the maximum amplitude of the acoustic oscillation pulse 5 applied to the container wall 3;

$K_3$ is a coefficient making allowance for the effect of the contact layer located between the container wall 3 (FIG. 1) and the acoustic transducer 2 upon the passage of the acoustic oscillation pulses 9 to said transducer 2 after being reflected from the inner surface of the container wall 3, as well as for the properties of the acoustic transducer 2 operating as a receiver; and $\epsilon$ is a coefficient (less than one) making allowance for attenuation of the acoustic oscillation pulse 5 passing twice through the container wall 3.

The amplitude $U_t$ of the maximum values of the pulse acoustic reverberation envelope 17, which is indicated by a dotted line on (FIG. 2c), decreases in each period T of application of the acoustic oscillation pulses 5 with the time t. This decrease can be with a fair approximation be described by the relationship:

$$U_t = \frac{K_3 B}{R}\left(\epsilon R \frac{1 - \frac{Z_1}{Z}}{1 + \frac{Z_1}{Z}}\right)^{\frac{t-\tau'}{\tau}}; \qquad (9)$$

where R is the reflection factor of the acoustic oscillation pulse 9 on the boundary between the inner surface of the container wall 3 and the acoustic transducer 2; and $\tau'$ is the duration of the leading edge of the pulse acoustic reverberation envelope 17.

The above relationship is valid for the time t satisfying the following inequality:

$$\tau + \tau' \leq t > \tau + \tau_2; \qquad (10)$$

The time $t = \tau + \tau'$ corresponds to the maximum $U_0$ of the pulse acoustic reverberation envelope 17, since it is evident from the expressions (8) and (9) that with such time $$U_{t=\tau+\tau'} = U_o; \qquad (11)$$

As the acoustic impedance $Z_1$ of the liquid solution is, in accordance with the expression (6), the function of $\phi_2(q)$ of the concentration q of this solution, the amplitude $U_t$ of the pulse acoustic reverberation envelope is also, in accordance with the just obtained expression (10), the function of said concentration q:

$$U_t = \phi_3(q); \qquad (12)$$

Thus, the pulse acoustic reverberation envelope 17 obtained at the output of the detector 16 (FIG. 1) carries information on the measured property of the fluid. In the discussed example of industrial application of the disclosed method and device for its realization this property is concentration q of the liquid. solution.

The pulse acoustic reverberation envelope 17 is fed from the output of the detector 16 to the input of the shaper 19 of the data-carrying electric signal 20 (FIG. 2e) which electrical parameter is proportional to the fluid property of interest. This data-carrying electric signal 20 is fed to the input of the measuring unit 23 in which it is converted into a standard electric signal proportional to the fluid property being measured. The output signal of the measuring unit 23 is supplied to the recorder 24. Depending on the conditions of measurements, the results can be obtained in two ways. Firstly, the results of measurements can be determined by a scale graduated in units of the fluid property being measured. For example, when measuring concentration of liquid solutions, the measurements are in g/l (gramm of the dissolved substance per liter of solution). In case the recorder 24 is made on of a relay, the result of measurements of a fluid property is determined by the presence or absence of deviations of the fluid property from its nominal value.

The data-carrying electric signal can be formed from the pulse acoustic reverberation envelope 17 (FIG. 2c) obtained in the detector 16 in several ways.

One is to determine the area S limited by the pulse acoustic reverberation envelope 17 and the zero level thereof and, then, to find the ratio of this area S to the time interval proportional to the time interval T (FIG. 2a) between two successively applied acoustic oscillations pulses 5 (FIG. 1).

This area S is defined fairly accurately for practical purposes and for the pulse acoustic reverberation envelope 17 by the expression:

$$S = 0.5\tau^1 U_o + \int_{\tau + \tau'}^{\tau + \tau_3} U_t \, dt; \tag{13}$$

Let us consider the function which is a part of the expressions (8) and (9) for $U_o$ and $U_t$ $$R_1 = (1 - Z_1/Z)(1 + Z_1/Z)^{-1}; \tag{14}$$

as a function of a variable:

$$\Delta Z_1 = Z_1 - Z_{01}; \tag{15}$$

The latter, as it is clear from the equation (6), is in its turn a function of the fluid property being measured, that is the concentration q of the liquid solution:

$$\Delta Z_1 = K_2 Z_{01} q; \tag{16}$$

It follows from the expressions (14) and (15) that:

$$R_1 = R_{01}\left(1 - \frac{2\Delta Z_1}{Z + \Delta Z_1 - \frac{Z_{01}^2}{Z}}\right); \tag{17}$$

In the just obtained equation $R_{01}$ is the function $R_1$ when the acoustic impedance $Z_1$ is equal to the initial acoustic impedance $Z_{01}$ of the fluid 6 (FIG. 1).

For example, where concentration q of the liquid solution is measured, $R_{01}$ is equal to the function $R_1$ when the acoustic impedance $Z_1$ is equal to the acoustic impedance $Z_{OI}$ of the solvent. In this case $$R_{01} = (1 - Z_{01}/Z)(1 + Z_{01}/Z)^{-1}, \tag{18}$$

In most practical cases the acoustic impedance of the container wall 3 is one order of magnitude more than the acoustic impedance $Z_1$ of the fluid 6 and its variations $\Delta Z_1$ that is $$Z_{01} << Z \text{ и } \Delta Z_1 << Z; \tag{19}$$

That is why the equation (17) can be given with a fair degree of accuracy in a simplier form;

$$R_1 = R_{01}(1 - 2\Delta Z_1/E); \tag{20}$$

When measuring the concentration q of liquid solutions and according to the equations (16) and (20) we get:

$$R_1 = R_{01}(1 - 2K_2 q Z_{01}/Z); \tag{21}$$

Hence, the maximum amplitude $U_o$ of the pulse acoustic reverberation envelope 17 and the running value $U_t$ of said envelope 17 are given in accordance with the relations (8), (9), (14), and (20) by the following equations:

$$U_o = \epsilon K_3 B R_{01}\left(1 - 2\frac{\Delta Z_1}{Z}\right); \tag{22}$$

$$U_t = \frac{K_3 B}{R}\left[\epsilon R R_{01}\left(1 - 2\frac{\Delta Z_1}{Z}\right)\right]^{\frac{t-\tau^1}{\tau}}; \tag{23}$$

On substituting these equations (22) and (23) for the maximum amplitude $U_o$ of the pulse acoustic reverberation envelope 17 (FIG. 2c) and the value $U_t$ of the amplitude of said envelope 17 in the expression (13) for the area S limited by said envelope 17 of pulse acoustic reverberation and its zero level, the equation becomes:

$$S = 0.5\tau' \epsilon K_3 B R_{01}\left(1 - \frac{2\Delta Z_1}{Z}\right) + \tag{24}$$

$$\frac{K_3 B}{R} \int_{\tau + \tau'}^{\tau + \tau_3} \left[\epsilon R R_{01}\left(1 - 2\frac{\Delta Z_1}{Z}\right)\right]^{\frac{t-\tau'}{\tau}} dt$$

or, after integrating $$S = \epsilon K_3 B \tau R_{01}\left(1 - \frac{\Delta Z_1}{Z}\right) \times \tag{25}$$

$$\left\{\frac{\left[\epsilon R R_{01}\left(1 - 2\frac{\Delta Z_1}{Z}\right)\right]^{\frac{\tau_3 - \tau'}{\tau}} - 1}{\ln\left[\epsilon R R_{01}\left(1 - \frac{2\Delta Z_1}{Z}\right)\right]} + \frac{\tau'}{2\tau}\right\};$$

The ratio A of said area S to the time interval $\Delta t$ proportional to the time interval T (FIG. 2a) between two successively applied pulses 5 (FIG. 1) of acoustic oscillations, which is an indication of the property of the fluid 6, according to the just obtained expression, amounts to:

$$A = \frac{\epsilon K_3 B R_{01} \tau}{K_4 T} \times \tag{26}$$

-continued $$\left\{ \frac{\left[\alpha\left(1-2\frac{\Delta Z_1}{Z}\right)\right]^{\frac{\tau_3-\tau^1}{\tau}}-1}{\ln\left[\alpha\left(1-2\frac{\Delta Z_1}{Z}\right)\right]} + \frac{\tau'}{2\tau} \right\}\left(1-2\frac{\Delta Z_1}{Z}\right)$$

where $K_4$ is the constant proportionally factor and $$\alpha = \epsilon RR_{01};  \qquad (27)$$

The above described operations, aimed at finding the area S limited by the pulse acoustic reverberation envelope 17 (FIG. 2c) and the zero level thereof and at determination of the ratio A of said area S to the time interval proportional to the time interval T between two successively applied pulses 5 (FIG. 1) of acoustic oscillations, are carried out in the shaper 19 of the data-carrying electric signal 20. Here the pulse acoustic reverberation envelope 17 is supplied from the output of the detector 16 of said envelope 17 via the emitter follower 22 to the input of the integrator 21 of the pulse acoustic reverberation envelope 17. In this case said integrator 21 forms the data-carrying electric signal 20 with an amplitude $E_o$ (FIG. 2e) given by the following equation:

$$E_o = K_5 A = \frac{K_6}{\ln\alpha + \ln\left(1-2\frac{\Delta Z_1}{Z}\right)} \times \qquad (28)$$

$$\left\{\alpha^\gamma\left(1-2\frac{\Delta Z_1}{Z}\right)^\gamma - 1 + \frac{\tau'}{2\tau}\left[\ln\alpha + \ln\left(1-2\frac{\Delta Z_1}{Z}\right)\right]\right\}\times\left(1-2\frac{\Delta Z_1}{Z}\right);$$

where $K_5$ and $K_6$ are proportionally factors:

$$K_6 = \frac{\epsilon K_3 K_5 B R_{01}\tau}{K_4 T}; \text{ and} \qquad (29)$$

$$\gamma = \frac{\tau_3-\tau'}{\tau}; \qquad (30)$$

The data-carrying electrical signal 20 is supplied from the output of the integrator 21 (FIG. 1) to the input of the measuring unit 23. The measuring unit 23 converts the data-carrying electric signal 20 having the amplitude $E_o$ proportional to the fluid property of interest into a standard electric signal of a specific shape in accordance with the measurement conditions. The standard electric signal is fed from the output of the measuring unit 23 to the recorder producing output information on the fluid property of interest in the required form.

When concentration q of a liquid solution is measured, for example, the standard signal is shaped from the difference signal between the running data-carrying signal having the amplitude $E_o$ and the reference signal having the amplitude $E_{oo}$. This reference signal is shaped in the measuring unit 23 itself and is set equal to the amplitude of the data-carrying signal $E_o$, if the container holds a solvent with the acoustic impedance $Z_{0l}$, that is when the concentration q and the increment $\Delta Z_1$ of acoustic impedance of the fluid, respectively, are equal to zero.

$$E_{00} = K_{06}\left(\frac{\alpha^\gamma-1}{\ln\alpha}+\frac{\tau'}{2\tau}\right); \qquad (31)$$

where $K_{06}$ is the value of $K_6$ with the initial values $B_o$ of the amplitude of the acoustic oscillation pulse 5 and the factor $B_{03}$ making allowance for variations of the contact layer between the container wall 3 and the acoustic transducer 2 and conversion properties of the acoustic transducer 2, when it operates as a receiver.

When measuring the concentration q of a liquid solution, the measuring unit 23 is built of a differential circuit. The standard signal $$E_U = E_{oo} - E_o; \qquad (32)$$

in this case amounts to a value dependent upon the variation $\Delta Z_1$ of acoustic impedance of the fluid 6 and the concentration q of the liquid solution, respectively:

$$E_U = \beta E_{00}\frac{\Delta Z_1}{Z}; \text{ or} \qquad (33)$$

$$E_U = \beta K_2\frac{Z_{01}}{Z}E_{00}q; \qquad (34)$$

where $\beta$ is the sensitivity factor of measuring the property of the fluid.

When variations $Z_1$ of acoustic impedance of the fluid, which are caused by the variations in the fluid property being measured, are weak, which is usually the case in practice, the fluid property measurement sensitivity factor $\beta$ is given by the expression:

$$\beta = \frac{K_6}{K_{06}E_{00}}\cdot\frac{dE_U}{d\left(\frac{\Delta Z_1}{Z}\right)_{\Delta Z \to 0}} \qquad (35)$$

where $\dfrac{dE_U}{d\left(\frac{\Delta Z_1}{Z}\right)}$ is the first derivative of the standard signal which is the function of the variable $\Delta Z_1/Z$ with respect to said variable.

The variable $E_U$ with respect to $\Delta Z_1/Z$ permits the following expression for the measurement sensitivity $\beta$ of the fluid property of interest:

$$\beta = 2\left\{\frac{\gamma\alpha^\gamma K_7 - 1}{\left[1+\frac{K_7\tau'}{2\tau}\right]\ln\alpha} + 1\right\} \qquad (36)$$

where $K_7 = \dfrac{\ln\alpha}{\alpha^\gamma - 1}$ \qquad (37)

The values of the factor $K_7$ for several values of $\alpha$ and $(\gamma\alpha^{65}K_z-1)\text{Cn}^{-1}\alpha$, when $\gamma$ is equal to 10, are given in Table 2.

Table 2

| $\alpha$ | 7 | 0.99 | 0.98 | 0.97 | 0.96 |
|---|---|---|---|---|---|
| $K_7$ | 0.1 | 0.1051 | 0.1104 | 0.1159 | 0.1218 |
| $(\gamma\alpha^\gamma K_7 - 1)\ln^{-1}\alpha$ | 5 | 4.93 | 4.86 | 4.78 | 4.70 |

The above described method of measuring properties of a fluid is simple to realize. It permits effective measuring when the amplitude B of the acoustic oscillation pulses 5 applied to the container wall 3 are constant, as well as the contact layer and piezoconversion properties of the acoustic transducer 2 operating as a receiver.

When these parameters are not stable, the value of the factor K multiplied by the amplitude B of the acoustic oscillation pulses 5 also changes, since it is dependent on said parameters. This results in the zero drift $\Delta E_U$ of the measurements of properties of the fluid 6, which is defined as the difference between the value $E_{oo}$ of the data-carrying electric signal 20 at $\Delta Z_1 = 0$ and the reference electric signal. This zero drift of measurements of the fluid property of interest amounts, with respect to the range of the fluid property being measured, to $$\Delta E_U = -\left(\frac{\Delta B}{B} + \frac{\Delta K_3}{K_3}\right)\frac{E_{oo}}{E_{um}} \tag{38}$$

where $\frac{\Delta B}{B_0}$ and $\frac{\Delta K_3}{K_{03}}$ are the relative variations of the amplitude B of the acoustic oscillation pulse 5 and the factor K making allowance for changes in the contact layer between the container wall 3 and the acoustic transducer 2 and changes in the conversion properties of the latter operating as a receiver; $E_{um}$ is the standard signal $E_U$ corresponding to the upper limit of the measured range of the fluid property variations.

The above mentioned variations $\Delta B$ and $\Delta K_3$ are equal to:

$$\Delta B = B - B_o; \tag{39}$$

$$\Delta K_3 = K_3 - K_{03}; \tag{40}$$

In order to eliminate this zero drift $\Delta E_U$ during measurements of the fluid properties, which is caused by the unstable amplitude of the acoustic oscillation pulse 5 (FIG. 1) applied to the container wall 3, the maximum amplitude $U_o$ (FIG. 2c) of the pulse acoustic reverberation envelope 17 is additionally measured and compared to the ratio A of the area S limited by this envelope 17 and its zero level to the time interval proportional to the time interval T (FIG. 2a) between two acoustic oscillation pulses 5 successively applied to the container wall 3.

For this purpose the second embodiment of the device is provided with the peak detector 25 (FIG. 3) of the pulse acoustic reverberation envelope 17 shaping the electric signal 26 equal in voltage to the maximum amplitude $U_o$ of said envelope 17. This signal is fed to the input of the emitter follower 27, the reference electric signal 28 being formed at the output thereof with an amplitude $$E_{00} = K_8 U_o \tag{41}$$

where $$K_8 = K_5 \tau / K_4 T \tag{42}$$

In this case the amplitude $E_{oo}$ of the reference signal follows any variations $\Delta K_3$ and $\Delta B$ of, respectively, the factor $K_3$ and the amplitude B of the acoustic oscillation pulse 5 applied to the container wall 3. In consequence, the zero drift of measurements of the fluid property of interest is ruled out, since the value $E_{O\Delta Z1 \to 0}$ and $E_{oo}$ are equal.

The zero drift being thus eliminated, the sensitivity factor of the fluid property measurements is $$\beta_1 = 2\left[\frac{K_7(\alpha^\gamma \cdot \gamma - \ln\alpha) - 1}{\left(1 + \frac{K_7\tau'}{2\tau}\right)\ln\alpha} + 1\right] \tag{43}$$

Since the disclosed device (FIG. 3) ensures effective elimination of the zero drift of the recorder 24, which is caused by the above mentioned instability of the amplitude of the acoustic oscillation pulse 5 applied to the container wall 3, it is predominantly employed in industrial production processes, where deviations of the fluid property of interest from a specified nominal value is to be recorded, e.g. in optimization systems for technological processes.

Figure 4:
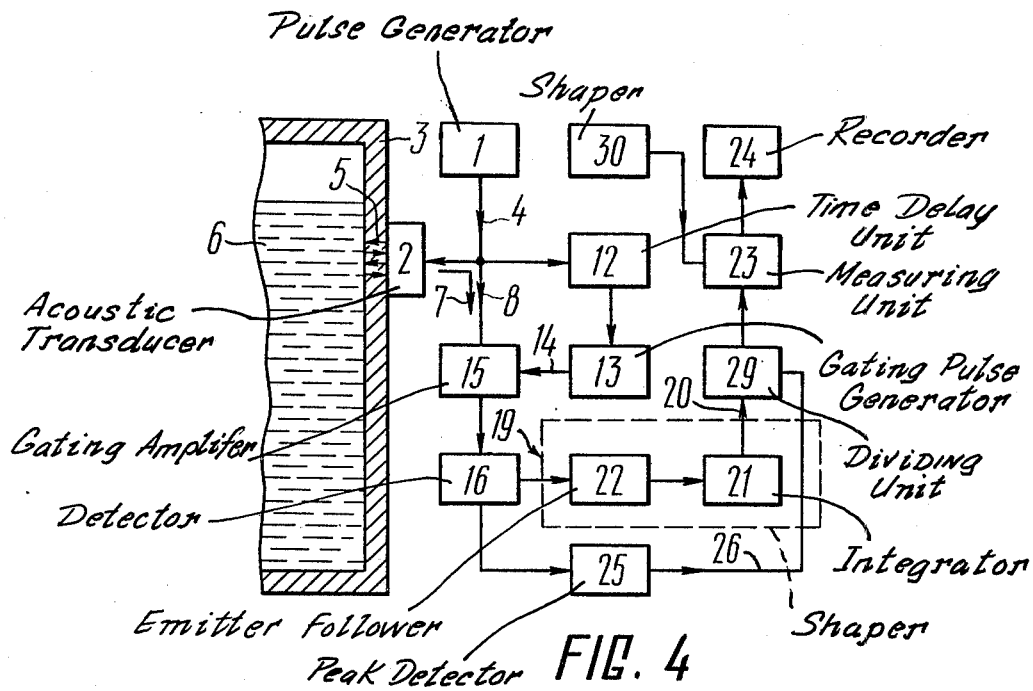
FIG. 4 is a block diagram showing the device of FIG. 1, provided with a peak detector of the pulse acoustic reverberation envelope, an electric signal dividing unit and a reference electric signal shaper in the electrical circuit of the proposed device, according to the invention.

In case it is required, apart from recording these variations of the fluid property of interest, to measure the value of these variations, a correction of measurement sensitivity variations should be furnished Such correction of variations in the sensitivity of measurements of the fluid property of interest, which are caused by the above mentioned instability of the amplitude of the pulse 5, is achieved in another embodiment of the device of FIG. 4. Here the signal 26 obtained at the output of the peak detector 25 is fed to the input of the unit 29 for dividing acoustic signals. Said signal 26 has an amplitude equal to the amplitude $U_O$ (FIG. 2c) of the pulse acoustic reverberation envelope 17. The other input of the dividing unit 29 (FIG. 4) is fed the data-carrying signal from the output of the shaper 19, which has the amplitude $E_O$. The output signal $E_o/U_o$ of the electric signal dividing unit 29 is:

$$E'_0 = K_g \frac{E_0}{U_0} = \frac{K_5 K_g \tau}{K_4 T}\left\{\frac{\alpha^\gamma\left(1 - 2\frac{\Delta Z_1}{Z}\right)^\gamma - 1}{\ln\left[\alpha\left(1 - 2\frac{\Delta Z_1}{Z}\right)\right]} + \frac{\tau'}{2\tau}\right\} \tag{44}$$

where $K_9$ is the constant factor dependent on the output characteristics of the electric signal dividing unit 29.

The signal $E_{0'}$ is supplied from the output of the electric signal dividing unit 29 to the measuring unit 23 built of a differential circuit, where said signal $E_{0'}$ is compared to the reference signal $E_{00'}$ supplied from the shaper 30. Said reference signal is set in advance equal in amplitude to the output signal of the electric signal dividing unit 29 at the initial value of the property of interest of the fluid 6. In this case the reference signal value is given by the expression:

$$E'_{00} = \frac{K_5 K_g \tau}{K_4 T}\left(\frac{\alpha - 1}{\ln\alpha} + \frac{\tau'}{2\tau}\right) \tag{45}$$

The output signal of the measuring unit 23, having the amplitude $E_u = E_{00'}E_{0'}$, is proportional to the variation of the acoustic impedance of the fluid 6 and, respectively, to the property being measured, e.g. concentration q of the liquid solution:

$$E_U = \beta_2 E_{00'} \Delta Z_1/Z; \tag{46}$$

Here the sensitivity factor $\beta_2$ of measurement of the fluid property of interest is given by the following expression:

$$\beta_2 = \frac{1}{E'_{oo}} \cdot \frac{dE_u}{d\left(\frac{\Delta Z_1}{Z}\right)} ; \quad (47)$$

and has the following value at low values of $\Delta Z_1$:

$$\beta_2 = 2 \frac{\gamma a^\gamma K_7 - 1}{\left(1 + K_7 \frac{\tau'}{2\tau}\right) \ln a} ; \quad (48)$$

The electric signal 20 carrying information on the properties of the fluid 6 can be also shaped by separating portions on the leading and trailing edges of one of the pulse acoustic envelopes 17, whose respective ends lie on two amplitude levels at least one order of magnitude less than the maximum amplitude $U_o$ of said envelope 17, and finding the time interval $\tau_4$ between said portions.

For better understanding of the method of measuring properties of a fluid, realized in the above described embodiments of the device, time charts are given in FIGS. 13a–13f, 14a–14h, 15a–i and 16a–16g.

Referring to FIGS. 13a–13f the ordinates are, respectively, the amplitudes of: the electric oscillation pulse 4 of the generator 1, the pulse acoustic reverberation envelope 17 with two amplitude limitation levels $E_1$ and $E_2$, the bidirectionally clipped pulse 32, the output signal 26 of the peak detector 25 of said envelope 17, the data-carrying signal 20 and the recorded signal.

Referring to FIGS. 14a–14k, the ordinates are, respectively, the amplitudes of: the electric oscillation pulse 4 of the generator 1, the pulse acoustic reverberation envelope 17 with two amplitude limitation levels $E_1$ and $E_2$, the bidirectionally clipped pulse 32, pointed voltage pulses generated in the differentiating unit 35, the output pulse 36 of the differentiating unit 35, the output signal 26 of the peak detector 25, the pulse 40 of a specified duration, pointed voltage pulses generated in the differentiating unit 41, the reference electric pulse 38, the data-carrying pulse and the electric signal 20.

Referring to charts FIGS. 15a–15i, the ordinates are, respectively, the amplitudes of: the electric oscillation pulse 4 of the generator 1, the pulse acoustic reverberation envelope 17, the first gating pulse 46, the pulse 48 corresponding to the first separated portion on the trailing edge of said envelope 17, the data-carrying electric signal 20 obtained at the output of the peak detector 49, the reference electric signal with the amplitude $E_4$ proportional to the maximum amplitude of the envelope 17, the second gating pulse 53, the pulse 55 corresponding to the second separated portion on the trailing edge of the envelope 17, and the amplitude $E_5$ of the direct current voltage obtained at the output of the peak detector 56 of said second separated portion.

Referring to FIGs. 16a–16g, the ordinates are, respectively, the amplitudes of: the electric oscillation pulse 4 of the generator 1, the first pulse acoustic reverberation envelope 17 which corresponds to the envelope 17 of the standard electric pulse 60, the second pulse acoustic reverberation envelope 18 corresponding to the envelope 18 of the standard electric pulse 63, and rectangular pulses whose duration is determined by the time difference between shaping of the standard pulses 60, 63 and 60', 63', respectively.

The unit 31 (FIG. 5) for limiting the pulse acoustic reverberation envelope 17 produced from said envelope 17 generates an electric pulse 32 with the duration $\tau_4$ (FIG. 13c) and the amplitude $U_1$. The leading and trailing edges of the pulse 32 correspond to two portions of the pulse acoustic reverberation envelope 17, the ends thereof being located on two amplitude levels $E_1$ and $E_2$ (FIG. 13b).

In this case the leading edge of this pulse is shaped at the instant $t_1$ counted from the moment when the acoustic oscillation pulses 5 (FIG. 5) are applied to the container wall 3 and given by the expression:

$$\tau_1 = \tau + \tau' \frac{E_1}{U_{oo}\left(1 - 2\frac{\Delta Z_1}{Z}\right)} ; \quad (49)$$

and the trailing edge is shaped at the moment $t_2$ counted in a similar manner:

$$t_2 = \tau' + \tau \frac{\ln\left(\alpha \frac{E_1}{U_{oo}}\right)}{\ln\left[\alpha\left(1 - 2\frac{\Delta Z_1}{Z}\right)\right]} \quad (50)$$

where $U_{oo} = K_3 BER_{o1}$; $\quad (51)$ is the maximum amplitude of the pulse acoustic reverberation envelope 17 at the initial acoustic impedance $Z_{oI}$ of the fluid 6 in the container, that is at $\Delta Z_1 = 0$.

The duration $\tau_4$ of the shaped electric pulse 32 equal to $t_2 - t_1$ amounts to a value dependent upon the variations $\Delta Z_1$ of the acoustic impedance of the fluid 6 and, respectively, upon the changes in the properties of said fluid:

$$\tau_4 = \tau\left\{\frac{\ln\left(\alpha \frac{E_1}{U_{oo}}\right)}{\ln\left[\alpha\left(1 - 2\frac{\Delta Z_1}{Z}\right)\right]} - 1\right\} + \quad (52)$$

$$\tau'\left[1 - \frac{E_1}{U_{oo}\left(1 - 2\frac{\Delta Z_1}{Z}\right)}\right]$$

Variation $\Delta \tau_4$ of the duration of this pulse, caused by the variation $\Delta Z_1$ of the acoustic impedance of the fluid 6, equal to $$\Delta \tau_4 = \frac{\delta \tau_4}{\delta\left(\frac{\Delta Z_1}{Z}\right)} \cdot \frac{\Delta Z_1}{Z} \quad (53)$$

amounts to $\Delta \tau_4 = \beta_3 \tau \frac{\Delta Z_1}{Z} \quad (54)$

Where $\delta \tau_4 / \delta(\Delta Z_1/Z)$ is the partial derivative of $\tau_4$ with respect to $\Delta_1/Z$, $\beta_3$ is the sensitivity factor of measurements of the fluid properties, which is given by the equation:

$$\beta_3 = \frac{1}{\tau} \cdot \frac{\delta \tau_4}{\delta\left(\frac{\Delta Z_1}{Z}\right)} = \tag{55}$$

$$2\frac{\ln\left(\alpha \frac{E_1}{U_{oo}}\right)}{\left(1 - 2\frac{\Delta Z_1}{Z}\right)\ln^2\left[\alpha\left(1 - 2\frac{\Delta Z_1}{Z}\right)\right]} - 2\frac{E_1}{\tau U_{oo}\left(1 - 2\frac{\Delta Z_1}{Z}\right)^2}$$

The factor $\beta_{03}$ of the initial measurement sensitivity, that is the factor $\beta_3$ at minor deviations of the acoustic impedance $Z_1$ from its initial value $Z_{OI}$, is given by the following expression:

$$\beta_{03} = 2\frac{\ln\left(\alpha \frac{E_1}{U_{oo}}\right)}{\ln^2 \alpha} - 2\frac{E_1 \tau'}{U_{oo}\tau} \tag{56}$$

The sensitivity factor $\beta_3$ of measurement of the fluid property of interest, similar to its initial value $\beta_{03}$, is a negative value, because as the acoustic impedance $Z_1$ grows, the duration $\tau_4$ of the electric pulse 32 produced by the unit 31 (FIG. 5) for limiting the pulse acoustic reverberation envelope 17 diminishes.

With typical parameters $$\alpha = 0.95;\ E_1/U_{oo} = 0.1;\ \tau'/\tau = 0.3 \tag{57}$$

$$\beta_{03} = -1829.8\ \beta_3 = \tag{58}$$

$$\frac{7829.7}{\left(1 - 2\frac{\Delta Z_1}{Z}\right)\left[1 - 19.502 \ln\left(1 - 2\frac{\Delta Z_1}{Z}\right)\right]} - \frac{0.06}{\left(1 - 2\frac{\Delta Z_1}{Z}\right)^2}$$

The relative sensitivity factor $\beta_{3g}$ of measurements of the liquid solution concentration, which is equal to the increment $\Delta \tau_4$ for a unit of the solution concentration q with respect to the time $\tau$ required for the acoustic oscillations to twice pass through the wall 3 of the container with the fluid of interest, is given in accordance with the equations (7) and (54) by the following equation:

$$\beta_{3g} = \frac{\Delta \tau_4}{\tau g} = \beta_3 K_2 \frac{Z_{01}}{Z} \tag{59}$$

The factor $\beta_{3g}$ and variations $\Delta \tau_4$ of the duration of the pulse 32 at the output of the unit 31 for limiting the pulse acoustic reverberation envelope 17, which corresponds to 1 g/l of variation in the concentration q of some weak water solutions held in a steel container whose wall thickness d is equal to 12 mm, for typical parameters (57) are given in Table 3.

Table 3

| Water Solutions of: | Aluminum Sulfate | Lithium Hydrate | Ammonia | Muriatic Acid |
|---|---|---|---|---|
| $-\beta_{3g}$, $G^{-1} \times 1$ | 0.0302 | 0.0148 | 0.00296 | 0.0207 |

Table 3-continued

| Water Solutions of: | Aluminum Sulfate | Lithium Hydrate | Ammonia | Muriatic Acid |
|---|---|---|---|---|
| $-\frac{\Delta \tau_4}{g}$, $mxG^{-1}1$ | 0.124 | 0.0607 | 0.0121 | 0.0849 |

The pulse 32 with the duration $\tau_4$ and the amplitude $U_1$ is supplied from the output of the unit 31 to the shaper 19 of the data-carrying electric signal 20, which is built of a circuit of an electric pulse length meter. In the embodiment of the device, shown in FIG. 5, such an electric pulse length meter is built of the integrator 21. The pulse 32 is fed to the input of this integrator 21 with a repetition period T (FIG. 13a) through the emitter follower 22 (FIG. 5) from the output of the unit 31 for limiting the pulse acoustic reverberation envelope 17.

The electric pulses 32 are converted in the integrator 21 into the direct current voltage with the amplitude $E_3$ (FIG. 13e) proportional to the duration $\tau_4$ and the constant amplitude $U_1$:

$$E_3 = (K_{10} U_1/T)\tau_4 \tag{60}$$

where $K_{10}$ is the proportionality factor.

The data-carrying signal 20 (FIG. 5) whose amplitude $E_3$ is proportional to the property of interest of the fluid 6 is fed to the measuring unit 23. In said unit 23 the data-carrying signal 20 is compared in terms of the amplitude to the output signal of the shaper 30 of the reference electric signal whose amplitude $E_{03}$ (FIG. 13f) is set equal to $$E_{03} = (K_{10} U_1/T)\tau_4 \tag{61}$$

where, in accordance with the equation (52), $$\tau_{04} = \tau\left[\frac{\ln\left(\alpha \frac{E_1}{U_{oo}}\right) - 1}{\ln \beta}\right] + \tau'\left(1 - \frac{E_1}{U_{oo}}\right) \text{ or} \tag{62}$$

$$\tau_{04} = \tau \frac{\ln \frac{E_1}{U_{oo}}}{\ln \alpha} + \tau'\left(1 - \frac{E_1}{U_{oo}}\right)$$

The difference signal $E_U = E_{03} - E_3$ is supplied to the recorder 24 which registers in the required form the presence or value of deviations of the property of interest of the fluid 6 in the container from the initial value thereof.

The above described embodiment of the device is predominantly used for monitoring the state and properties of the fluid in optimization systems for technological processes as well as for detecting the boundary of media, such as gas-liquid or liquid-liquid.

Variations in the initial value $U_{oo}$ of the maximum amplitude of the pulse acoustic reverberaton envelope 17 accompanied by some relations of parameters of the fluid 6 and of the acoustic oscillation pulse 5 applied to the container wall 3 may result in changes in the sensitivity of measurements of the fluid properties, e.g. the concentration q of liquid solutions. The ratio $\theta_1$ of the value $\Delta \beta_3/\beta_3$ of the relative change $\beta_3$ caused by the change in the initial value $U_{oo}$ of the maximum amplitude of the pulse acoustic reverberation envelope 17 to the value $\Delta U_{oo}/U_{oo}$ of the relative change of the value $U_{oo}$ of the maximum amplitude of this envelope 17 can be given as follows:

$$\theta_1 = \frac{U_{oo}}{\beta_3} \cdot \frac{\delta\beta_3}{\delta U_{oo}} \qquad (63)$$

where $\frac{\delta\beta_3}{\delta U_{oo}}$ is the partial derivative of the factor $\beta_3$ of sensitivity of measurements of the fluid properties with respect to the initial value $U_o$ of the maximum amplitude of the pulse acoustic reverberation envelope 17.

The partial derivative of $\beta_3$ with respect to $U_{oo}$ amounts to:

$$\frac{\delta\beta_3}{\delta U_{oo}} = \frac{2}{U_{oo}\left(1-2\frac{\Delta Z_1}{Z}\right)} \left\{ \frac{\tau' E_1}{\tau U_{oo}\left(1-2\frac{\Delta Z_1}{Z}\right)} - \ln^{-2}\left[\alpha\left(1-2\frac{\Delta Z_1}{Z}\right)\right]\right\}; \qquad (64)$$

Taking into account this value, the equation (62) for the ratio $\theta_1$ of relative changes of the factor $\beta_3$ of sensitivity of measurements of properties of the fluid 6 and the value $U_{oo}$ will be:

$$\theta_1 = \frac{1 - a_1}{a_1 - \ln\left(\alpha\frac{E_1}{U_{oo}}\right)}; \qquad (65)$$

where $$a_1 = \frac{\tau' E_1 \ln^2\left[\alpha\left(1-2\frac{\Delta Z_1}{Z}\right)\right]}{\tau U_{oo}\left(1-2\frac{\Delta Z_n}{Z}\right)}; \qquad (66)$$

Since the typical values $\alpha$, $\tau'/\tau$ and $E_1 W_{oo}$, e.g. in accordance with the equation (57), $$a_1 \ll 1 \ u \ a_1 \ll \ln(\alpha E/U_{oo}); \qquad (67)$$

The equation (65) for the ratio $\theta_1$ of relative changes of the sensitivity factor $\beta_3$ of measurements of the fluid properties and the value $U_{oo}$ becomes:

$$\theta_1 = -\ln^{-1}(\alpha E_1/U_{oo}); \qquad (68)$$

It follows from the equation (68) that, when the value $E_1$ of the lower amplitude limitation level of the pulse acoustic reverberation envelope 17 is selected less than $U_{oo}/\alpha 1$ (where e is the base of the natural logarithm), the relative variation of sensitivity of the fluid property measurement does not exceed the relative variation of the initial value $U_{oo}$ of the maximum amplitude of the pulse acoustic reverberation envelope 17. Hence, for typical values of parameters $\alpha$ and $E/U_{oo}$ of the equation (57) a five percent change in the value $U_{oo}$ results in a 2.3% variation of the sensitivity of the fluid property measurement.

In order to eliminate the error caused by the above mentioned variation of the sensitivity of the fluid property measurement, owing to the instability of the value $U_{oo}$, the lower of the two amplitude limitation levels of the envelope 17, which has the amplitude $E_1$, is set variable in proportion to the variations of the maximum amplitude $U_o$ of the pulse acoustic reverberation envelope 17. In this case the peak detector 25 (FIG. 6) of the pulse acoustic reverberation envelope is incorporated into the device for the fluid property measurement in order to adjust the lower amplitude level of said separated portions of the pulse acoustic reverberation envelope 17. The direct current signal 26 (FIG. 13d) is formed at the output of the peak detector 25 in this case, having an amplitude equal to $U_{oo}(1 - 2\Delta Z_1/Z)$. Said signal 26 is supplied to the emitter follower 27 (FIG. 6) and a control signal is obtained at the output thereof, with an amplitude $$E_1 = a_2 U_{oo}(1 - 2\Delta Z_1/Z); \qquad (69)$$

where $a_2$ is the proportionality factor.

The control signal $E_1$ is further supplied to the unit 33 for cutting off the envelope 17 at the lower amplitude level and is used therein to limit said envelope 17 of pulse acoustic reverberation at said lower level. In this case the duration $\tau_4$ (FIG. 13, chart "c") of the pulse 32 produced by the cut-off unit 33 (FIG. 6) is given by the equation $$\tau_4 = \frac{\tau \ln a_2}{\ln\left[\alpha\left(1-2\frac{\Delta Z_1}{Z}\right)\right]} + \tau'(1 - a_2) \qquad (70)$$

The difference signal $E_u = E_0 - E_3$ shaped in the measuring unit 23 in accordance with the equations (60) and (61) amounts to $$E_U = (K_{10}U_1/E)_{04} - \tau_4); \qquad (71)$$

or taking into account the equality $$\tau_{04} = \frac{\tau \ln a_2}{\ln \alpha} + \tau^1(1 - a_2)$$

proceding from the equation (70), $$E_u = \frac{K_{10}\tau U_1}{T} \cdot \frac{\ln a_2 \ln\left(1 - 2\frac{\Delta Z_1}{Z}\right)}{\ln \alpha \cdot \ln\left[\alpha\left(1 - 2\frac{\Delta Z_1}{Z}\right)\right]}; \qquad (72)$$

the sensitivity factor $\beta_4$ of measurement of the property of interest of the fluid 6 in the container (FIG. 6) in the above described variant of the method and respective embodiment of the device amounts to a value independent of the initial value $U_{oo}$ of the maximum amplitude of the pulse acoustic reverberaton envelope 17:

$$\beta_1 = \frac{1}{\tau} \cdot \frac{\delta \tau_4}{\delta\left(\frac{\Delta Z_1}{Z}\right)} = \qquad (73)$$

$$\frac{2\ln a_2}{\left(1 - 2\frac{\Delta Z_1}{Z}\right)\ln^2\left[\alpha\left(1 - 2\frac{\Delta Z_1}{Z}\right)\right]}$$

The electric signal carrying information on the properties of the fluid is also shaped by separating a portion on the trailing edge of one of the pulse acoustic reverberation envelopes 17, whose ends are located on two amplitude levels $E_1$ (FIG. 14b) and $E_2$ at least one order of magnitude less than the maximum amplitude $U_o$ of this envelope 17, by shaping the electric pulse 36 (FIG. 14a) corresponding to the separated portion, generating the reference electric pulse 38 (FIG. 14i) at the instant of time, which corresponds to one of the positions of the shaped electric pulse 36 within the operating measurement range, and measuring the time interval between said pulses.

In this case the electric pulse 32 is shaped by means of the unit 31 (FIG. 7) for limiting the pulse acoustic reverberation envelope 17 on two amplitude levels. The trailing edge of the pulse 32 (FIG. 14c) corresponds to the portion of the trailing edge of said envelope 17, whose ends are located on two amplitude levels $E_1$ and $E_2$ (FIG. 14b). The trailing edge is formed at the instant $t_2$ defined by the equation (50). The shaped pulse 32 is supplied to the differentiating unit 35 (FIG. 7), where, after differentiation, it is converted into two pointed voltage pulses (FIG. 14d) corresponding to its leading and trailing edges. The trailing pointed pulse is used to shape at the output of the unit 35 the pulse 36 (FIG. 14e) spaced from the moment of the beginning of application of the acoustic oscillation pulse 5 (FIG. 7) to the container wall 3 by the time $t_2$. The pulse 36 is then fed to the input of the measuring unit 23. The reference electric pulse 38 (FIG. 14i) is supplied to the other input of the measuring unit 23. This reference electric pulse 38 is obtained with a time delay equal to $\tau_5$ at the output of the electric pulse time delay unit 37 (FIG. 7) of the generator 1. At the same time the electric pulses 4 of the generator 1 are supplied to the input of the shaper 39 of pulses of a specified duration, which is a part of the time delay unit 37. The shaper 39 produces pulses 40 (FIG. 14g) having a duration $\tau_5$ which is set equal to one of the values $t_{02}$ of the time $t_2$ of shaping the electric pulse 36 (FIG. 14e) within the operating range for measuring the property of the fluid 6 in the container. Such value can be the time $t_2$ at the initial value $Z_{01}$ of the acoustic impedance of the fluid, that is $$\tau_5 = t_{02} = \frac{\tau \ln\left(\alpha \frac{E_1}{U_{00}}\right)}{\ln \alpha} + \tau^1 \tag{74}$$

The pulses 40 are delivered from the output of the shaper 39 (FIG. 7) to the differentiating unit 41. After differentiating each pulse 40 is converted into pointed voltage pulses (FIG. 14h) corresponding to the leading and trailing edges thereof. The differentiating unit 41 (FIG. 7) converts the trailing pointed pulse into the reference pulse 38 (FIG. 14i) delayed with respect to the moment of application of the acoustic oscillation pulse 5 (FIG. 7) to the container wall 3 for the time $\tau_5$.

In response to the electric pulse 36 and the reference electric pulse 38 passed to the inputs of the measuring unit 23, said measuring unit 23 shapes a rectangular electric pulse (FIG. 14k). This rectangular pulse has the amplitude $U_2$ and the duration $\tau_6$ equal to the time interval between the electric pulse 36 and the reference electric pulse 38:

$$\tau_6 = t_{02} - t_2 = \frac{\tau \ln\left(\alpha \frac{E_1}{U_{00}}\right) \cdot \ln\left(1 - 2\frac{\Delta Z_1}{Z}\right)}{\ln \alpha \cdot \ln\left[\alpha\left(1 - 2\frac{\Delta Z_1}{Z}\right)\right]} \tag{75}$$

The duration $\tau_6$ of the shaped rectangular pulse, as follows from the equation (75), is proportional to the variations $\Delta Z_1$ of the acoustic impedance of the fluid 6 and, respectively, to the property of interest of said fluid. The sensitivity factor $\beta_5$ of measurements of the fluid properties is here given by the expression:

$$\beta_5 = \frac{1}{\tau} \cdot \frac{\delta \tau_6}{\delta\left(\frac{\Delta Z_1}{Z}\right)} = \tag{76}$$

$$\frac{2 \ln \frac{U_{00}}{\alpha E_1}}{\left(1 - 2\frac{\Delta Z_1}{Z}\right) \ln^2\left[\alpha\left(1 - 2\frac{\Delta Z_1}{Z}\right)\right]}$$

As far as its absolute value is concerned the factor $\beta_5$ differs but slightly from the factor $\beta_4$ of sensitivity of the fluid property measurement. Its general values for typical parameters $\alpha$ and $E_1/U_{oo}$ are given in the equations (57) and for measurements of concentrations of some solutions in the Table 2.

In case a digital unit is used as the recorder 24, the above mentioned rectangular pulse (FIG. 14j) is directly employed as the standard electric signal. In this case the recorder 24 (FIG. 7) indicates on the display and the punched card digital information on the duration $\tau_6$ of the pulse being supplied thereto and, respectively, on the property of the fluid, e.g. its concentration q.

When an analogue recorder 24 is employed and produces analogue information, the rectangular electric pulses are converted in the measuring unit 23 into the direct current standard signal with the voltage $E_3$ proportional to the duration $\tau_6$ of the rectangular pulses. When converted by integration, the voltage $E_3$ (FIG. 14e) amounts to:

$$E_3 = K_{11} U_2 \tau_6 / T \tag{77}$$

Figure 7:
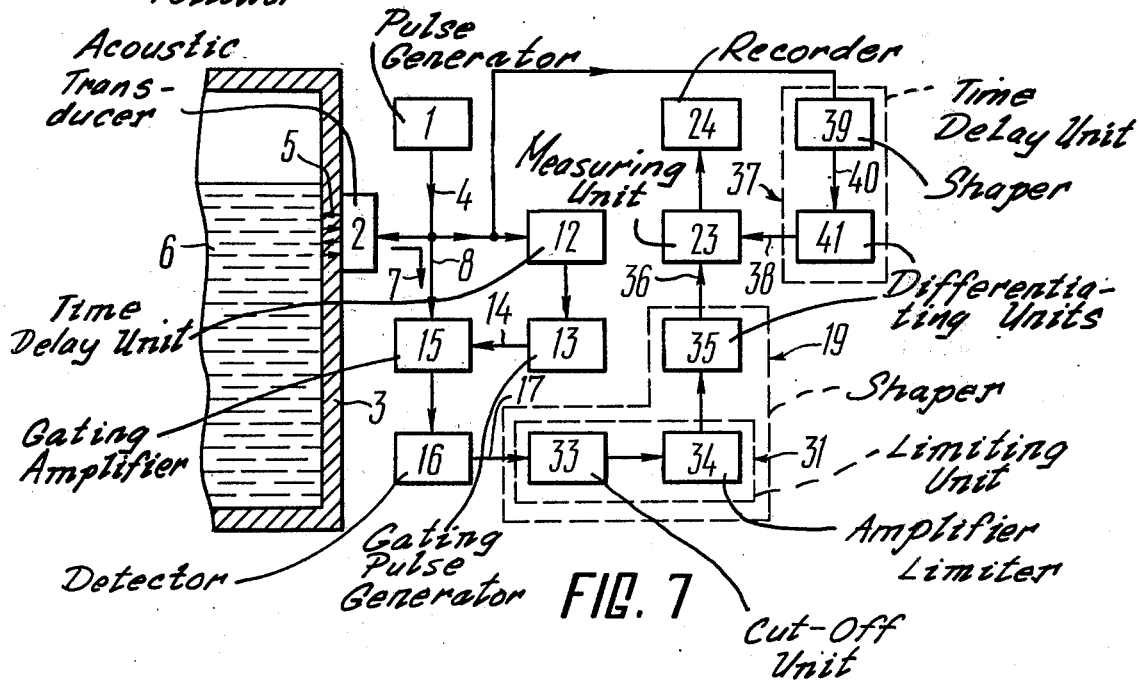
FIG. 7 is a block diagram showing the device of FIG. 1, featuring a unit for limiting the pulse acoustic reverberation envelope, a differentiating unit, an electric pulse time delay unit and a time interval measuring unit in the electrical circuit of the proposed device, according to the invention.

The above described embodiment of the device of FIG. 7 is mainly used to determine the presence and the sign of the fluid property deviations from its initial value, as well as for discrete indication of the liquid media levels.

This embodiment of the device can be, in addition, used to determine the value of said deviation of the fluid property being measured from its initial value, when variations in time of the initial value $U_{oo}$ of the maximum amplitude of the pulse acoustic reverberation envelope 17 are slight. In case variations in time of the value $U_{oo}$, caused by some relations of the device parameters, are significant, the zero drift of the fluid property measurement may appear. This zero drift may be caused by the instability of the value $t_{02}$ owing to, for example, variations in the amplitude B of the acoustic oscillation pulse 5 applied to the container wall 3 and, consequently, changes of the value $U_{oo}$.

The ratio $\theta_2$ of the measurement zero drift to the range $\Delta Z_1/Z$ of the measured variations in the acoustic impedance of the fluid property per unit of a relative change in the initial value $U_{oo}$ of the amplitude of the pulse acoustic reverberation envelope 17 can be described by the following equation:

$$\theta_2 = \frac{U_{00}\frac{\delta t_{02}}{\delta U_{00}}}{\delta\left(\frac{\Delta Z_1}{Z}\right)_{\Delta Z_1 \to 0}} = \frac{U_{00}\frac{\delta t_{02}}{\delta U_{00}}}{\beta_{05}\tau} \quad (78)$$

where $\beta_{05}$ is the initial value of the sensitivity factor $\beta_5$ of the fluid property measurement:

$$\beta_{05} = \frac{2\ln\left(\alpha\frac{E_1}{U_{00}}\right)}{\ln^2 \alpha} \quad (79)$$

Since, taking into account the equation (74), $$\frac{\delta t_{02}}{\delta U_{00}} = -\frac{\tau}{U_{00}\ln\alpha} \quad (80)$$

substitution of the value $\beta_{05}$ from the equation (79) and substitution of the obtained value $2t_{02}/zU_{00}$ to the equation (78) leads to:

$$\theta_2 = \frac{\ln\alpha}{2\ln\left(\alpha\frac{E_1}{U_{00}}\right)} \quad (81)$$

It follows from the obtained equation that the zero drift can be brought down to a negligible value, if the parameter $\alpha$ is close enough to one. Thus, for $\alpha = 0.98$ and $E_1/U_{oo} = 0.1$ the value $\theta_2$ is equal to 0.00428. In this case the relative change of the value $U_{oo}$ by 5% results in the measurement zero drift corresponding to a change of the ratio of the acoustic impedance $Z_1$ of the fluid to the acoustic impedance of the container wall 3 by a minor quantity equal to $2.14 \times 10^{-4}$. In terms of measuring the concentration q, of e.g. water solution of aluminum sulphate, the zero drift $\Delta g_o$ in response to a 5a % change of $U_{oo}$ amounts to $\theta_2/20K_2$ which is less than 0.5 g/l.

Practically speaking, complete elimination of the zero drift of the fluid property measurements is achieved by shaping the reference electric signal 38 (FIG. 14i) with the time delay $\tau_5$ proportional to the variation of the maximum amplitude $U_o$ of the pulse acoustic reverberation envelope 17.

For this purpose the peak detector 25 (FIG. 8) shapes the direct current electric signal 26 (FIG. 14f) from the pulse acoustic reverberation envelope 17 supplied from the output of the detector 16 of said envelope 17.

This electric signal 26 having the amplitude $U_o = U_{oo}(1-2\Delta Z_1/Z)$ is fed through the emitter follower 27 (FIG. 8) to the input of the unit 42 controlling the time delay $\tau_s$ of electric pulses. The output signal of the unit 42 is fed to the controlled input of the shaper 39 of the pulses 40 whose duration $\tau_5$ is connected with the electric signal 26 in the following manner:

$$\tau_5 = \tau_{05} + a_3 U_o \quad (82)$$

where
$\tau_{05}$ is the direct component of the time delay,
$a_3$ is the time delay proportional adjustment factor.

The reference electric pulse 28, shaped from the pulse 40 in the differentiating unit 41, has a time delay with respect to the moment of application of the acoustic oscillation pulse 5 to the container wall 3 equal to the duration $\tau_5$ of the pulse 40 (FIG. 14g).

The rectangular pulse shaped in the measuring unit 23 (FIG. 8) in response to the electric pulse 36 (FIG. 14e) and the reference electric pulse 38 (FIG. 14i) supplied to its inputs have a duration of:

$$\tau_6 = \tau_5 - t_2 = \tau_{05} + a_3 U_0 - \frac{\tau\ln\left(\alpha\frac{E_1}{U_{00}}\right)}{\ln\alpha} \quad (83)$$

This duration, like in the previous embodiment of the device, is proportional to the variations $\Delta Z_1$ of the acoustic impedance of the fluid 6 and, consequently, to the variations of the property of interest of said fluid, e.g. the concentration q of the liquid solution.

The direct component $\tau_{05}$ of the time delay and the time delay proportional adjustment factor $a_3$ are found by solving the following system of simultaneous equations:

$$\tau_{6\Delta Z_1 \to 0} = \tau_{05} + a_3 U_{00} - \frac{\tau\ln\left(\alpha\frac{E_1}{U_{00}}\right)}{\ln\alpha} = 0 \quad (84)$$

$$\frac{\delta\tau_6}{\delta U_{00\Delta Z_1 \to 0}} = a_3 + \frac{\tau}{U_{00}\ln\alpha} = 0 \quad (85)$$

As the value $U_{oo}$ is thought to be variable within certain limits (usually not more than several percent), in solving these equations $U_{ooo}$ equal to the initial value of $U_{oo}$ is taken instead of $U_{oo}$. In this case $$a_3 = -\frac{\tau}{U_{000}\ln\alpha} \quad (86)$$

$$\tau_{05} = \frac{\tau}{\ln\alpha}\left[1 + \ln\left(\alpha\frac{E_1}{U_{000}}\right)\right] \quad (87)$$

Taking into consideration the obtained values $a_3$, $\tau_{05}$ and $U_o$ obtained from the equation (22), the duration of the rectangular pulse (chart "j") shaped in the measuring unit 23 (FIG. 8) amounts, in conformity with the expression (83) to the following:

$$\tau_6 = \frac{\tau}{\ln\alpha}\left[1 - \frac{U_{00}}{U_{000}}\left(1 - 2\frac{\Delta Z_1}{Z}\right) + \frac{\ln\left(\alpha\frac{E_1}{U_{00}}\right)\ln\left(1 - 2\frac{\Delta Z_1}{Z}\right) + \ln\alpha\ln\frac{U_{00}}{U_{000}}}{\ln\left[\alpha\left(1 - 2\frac{\Delta Z_1}{Z}\right)\right]}\right] \quad (88)$$

The sensitivity factor $\beta_6$ of the fluid property measurement is expressed by the equation:

$$\beta_6 = \frac{1}{\tau} \cdot \frac{\delta\tau_6}{\delta\left(\frac{\Delta Z_1}{Z}\right)} = \quad (89)$$

-continued
$$\frac{2 \ln \frac{U_{00}}{\alpha E_1}}{\left(1 - 2\frac{\Delta Z_1}{Z}\right) \ln^2\left[\alpha\left(1 - 2\frac{\Delta Z_1}{Z}\right)\right]} + \frac{2 U_{00}}{U_{000} \ln \alpha}$$

The initial value $\beta_{06}$ of the sensitivity factor of the fluid property measurement, equal to the value $\beta_6$ at $Z_1 = 0$ and $V_{oo} = U_{ooo}$, amounts to:

$$\beta_{06} = \frac{2}{\ln \alpha}\left(1 + \frac{\ln \frac{U_{00}}{\alpha E_7}}{\ln \alpha}\right) \text{ or} \tag{90}$$

$$\beta_{06} = 2 \ln^{-2} d \cdot \ln \frac{U_{00}}{E_1}$$

It follows from these equations that the measurement sensitivity here differs also insignificantly from the sensitivity of the property measurement of the fluid 6 in the container for the previously described embodiment of the device whose circuit is shown in FIG. 5. Thus, for $\alpha = 0.95$ and $E_1/U_{oo} = 0.1$ the measurement sensitivity factor $\beta_{03}$ varies from 1829.8 to 1791.2, that is by 2.1% only.

With practically preserved measurement sensitivity, the zero drift here is reduced more than one order of magnitude. The ratio $\theta_3$ of the measurement zero drift to the range $\Delta Z_1/Z$ of measured variations of the acoustic impedance of the fluid 6 per unit of relative change of the initial value $U_{oo}$ of the amplitude of the pulse acoustic reverberation envelope 17 (FIG. 8) amounts to:

$$\theta_3 = U_{00}\beta_{06}^{-1}\tau^{-1}\frac{\delta\tau_6}{\delta U_{00} \Delta Z_1 \to O} \tag{91}$$

The partial derivative with respect to $U_{oo}$ of the duration $\tau_6$ of the pulse shaped in the measuring unit 23 with $\Delta Z_1$ tending to zero looks as follows, in accordance with the equation (88):

$$\frac{\delta\tau_6}{\delta U_{00} \Delta Z_1 \to O} = \frac{\tau}{U_{00} \ln \alpha} - \frac{\tau}{U_{00} \ln \alpha} \tag{92}$$

In conformity with this equation (92) and the factor $\beta_{06}$ from the expression (90) the ratio $\theta_3$ can be given in the following way:

$$\theta_3 = \frac{\ln \alpha}{2 \ln \frac{U_{00}}{E_1}}\left(1 - \frac{U_{00}}{U_{000}}\right) \tag{93}$$

Figure 8:
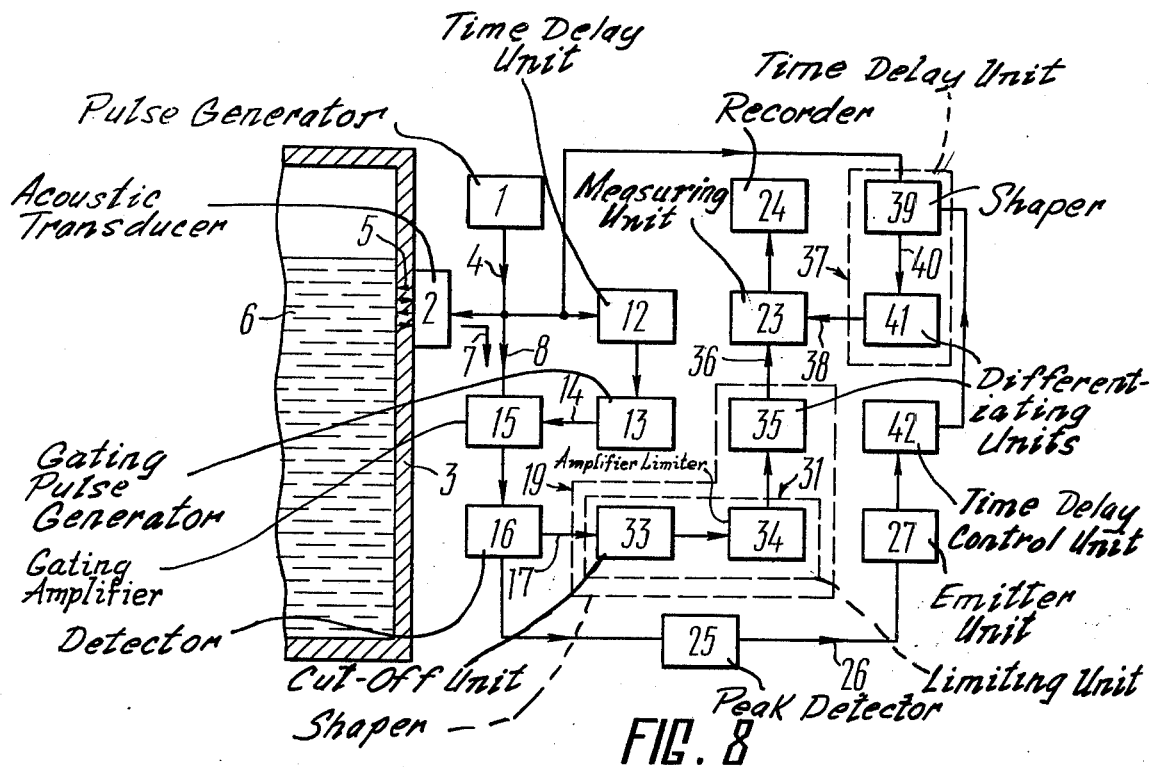
FIG. 8 is a block diagram showing the device of FIG. 7, featuring a peak detector of the pulse acoustic reverberation envelope and an electric pulse time delay control unit in the electrical circuit of the proposed device, according to the invention.

It follows from the comparison between the equations (81) and (93) with respect to values $\theta_2$ and $\theta_3$ that, if time delay adjustment is provided in the embodiment of FIG. 8, the zero drift, all other things being equal, is reduced by $$(1 - \frac{U_{00}^{-1}}{U_{000}})(1 - \ln \alpha \cdot \ln^{-1}\frac{U_{00}^{-1}}{E_7})$$

times. In particular, with a 5% change of $U_{oo}$ the measurement zero drift is reduced by about 20 times and amounts to a negligible value having almost no effect on the accuracy of measurements.

The electric signal carrying information on the properties of the fluid can be also produced by separating a portion on the trailing edge of one of the pulse acoustic reverberation envelopes 17, said portion having the duration $\tau_7$ (FIG. 15b) approximately equal to the value $\tau$ of the time required for the acoustic oscillation pulse 5 (FIG. 8) to pass twice through the container wall 3 and spaced from the leading edge of said envelope 17 a distance divisible by at least one order of magnitude of the value $\tau$ of the time required for the acoustic oscillation pulse 5 to pass twice through the container wall 3, and finding the maximum amplitude $U_3$ of the envelope 17 on this portion.

The electric signal carrying information on the fluid properties is shaped in this manner in the embodiment whose circuit is shown in FIG. 9.

Here a portion is separated by means of the gating amplifier 47 controlled by the gating pulse 46 (FIG. 15c) on the trailing edge of the pulse acoustic reverberation envelope 17 as an individual pulse 48 (15d).

The gating pulse 46 is produced by the second generator 45 (FIG. 9) triggered by the pulse 4 (FIG. 15a) fed from the generator 1 (FIG. 9) with a time delay (FIG. 15c) produced by the second electric pulse time delay unit 44 (FIG. 9). The value $\tau_8$ of the time delay is set divisible by the value $\tau$ of the time required for the acoustic oscillation pulse 8 to pass twice through the container wall 3:

$$\tau_8 = B_1\tau; \tag{94}$$

where $b_1$ is the divisibility factor equal to a whole number.

The duration $\tau_7$ of the gating pulse 46 (FIG. 15c) is in this case set close to said value $\tau$ of th double time required for the passage of the acoustic oscillation pulse 5.

The pulse 48 (FIG. 15d) corresponding to the separated portion of the pulse acoustic reverberation envelope 17 has a duration equal to the duration $\tau_7$ of the gating pulse 46 (FIG. 15c) and the amplitude $U_4$ proportional to the amplitude $U_3$ of the separated portion of said envelope 17.

In this case $$U_4 = K_{12} U_3, \tag{95}$$

where $K_{12}$ is the proportionality factor.

The maximum amplitude $U_4$ of the pulse 48 corresponding to the separated portion of the trailing edge of the pulse acoustic reverberation envelope 17 depends upon the variation $\Delta Z_1$ of the acoustic impedance of the fluid in the following way:

$$U_4 = K_{12}U_{00}\alpha^{B_1-1}\left(1 - 2\frac{\Delta Z_1}{Z}\right)^{B_1} \tag{96}$$

The pulse 48 whose amplitude $U_4$ is the function of the measured property of the fluid 6 is supplied from the output of the gating amplifier 47 (FIG. 9) to the input of the peak detector 49. The detector 49 converts the supplied pulse 48 into the data-carrying electric signal 20 in the form of a direct current voltage (FIG. 15e). This voltage has the amplitude $E_3$ equal to the amplitude $U_4$ of said pulse 48.

The data-carrying electric signal 20 is passed from the output of the peak detector 49 (FIG. 9) to the measuring unit 23 where its amplitude is compared to that of the reference electric signal having the amplitude $E_4$ (FIG. 15f) delivered from the shaper 30. The difference signal $E_U = E_4 - E_3$ is supplied from the output of the measuring unit 23 to the recorder 24 registering the property of the fluid 6 filled in the container.

The sensitivity factor $\beta_7$ of the fluid property measurement is here defined by the following equation:

$$\beta_7 = \frac{1}{U_{004}} \frac{\delta E_U}{\delta\left(\frac{\Delta Z_1}{Z}\right)} = -\frac{1}{U_{004}} \frac{\delta U_4}{\delta\left(\frac{\Delta Z_1}{Z}\right)} \quad (97)$$

where $U_{004}$ are the values $U_4$ at $\Delta Z_1 = 0$ and $\Delta U_{00} - 0$.
Taking into account that $$\frac{\delta U_4}{\delta\left(\frac{\Delta Z_1}{Z}\right)} = -2B_1 K_{12} U_{00}\left[\alpha\left(1 - 2\frac{\Delta Z_1}{Z}\right)\right]^{B_1 - 1} \quad (98)$$

$$U_{004} = K_{12} U_{000} \alpha^{B_1 - 1} \quad (99)$$

The equation (97) for the factor $\beta_7$ will be:

$$\beta_7 = 2B_1 \frac{U_{00}}{U_{000}} \left(1 - 2\frac{\Delta Z_1}{Z}\right)^{B_1 - 1}; \quad (100)$$

Employment of the above described embodiment of the device permits effective control of the dividing boundary between two immiscible liquids, discrete indication of the liquid level and solution of other technical problems.

Monitoring the presence of and measuring deviations of the property of the fluid 6 from its initial value, e.g. the concentration q of liquid solutions, can also be performed in this embodiment of the device provided the initial value $U_{oo}$ of the maximum amplitude of the pulse acoustic reverberation envelope 17 is stable. Instability of $U_{oo}$ results in the zero drift of the fluid property measurements, which amounts to $E_3 \Delta U_{oo}/E_u U_{oo}$ (Here $\Delta U_{oo}/U_{oo}$ is the relative variation of $U_{oo}$).

Complete elimination of the zero drift of the fluid property measurements, which is caused by instability of $U_{oo}$ owing to, for example, and unstable amplitude of the acoustic oscillation pulses 5 applied to the container wall 3 can be achieved here by separating an additional portion of the pulse acoustic reverberation envelope 17 between its main portion and the leading edge, which is spaced from the main portion of said envelope 17 a distance divisible by the value $\tau$ of the time required for the acoustic oscillation pulse 5 to pass twice through the container wall 3, and a reference electrical signal is shaped of the separated additional portion of the envelope 17.

Such shaping of the reference electrical signal, which permits elimination of the zero drift in measuring the properties of the fluid 6, is realized in the embodiment of FIG. 10 in the following manner.

The second gating amplifier 54 of the amplitude of the pulse acoustic reverberation envelope 17, which is controlled by the gating pulses 53, has an additional portion is separated on the trailing edge of said envelope 17, the pulse 55 (FIG. 15h) corresponding to said portion. This portion is located between the main portion of the envelope 17 located within the time interval $\tau_8 - (\tau_8 + \tau_7)$ and the leading edge thereof. The pulse 53 is produced by the third generator 52 (FIG. 10) of gating pulses, which is triggered by the electric pulses 4 delivered from the generator 1 and fed through the third electric pulse time delay unit 51, delaying said pulses for the time $\tau_9$. This delay is set divisible by the time $\tau$ of the double time required for the acoustic oscillation pulse 5 to pass through the container wall 3:

$$\tau_9 = B_2 \tau, \quad (101)$$

where $b_2 = 1; 2 \ldots$ is the divisibility factor.

The duration $\tau_{10}$ of the gating pulse 53 (FIG. 15, chart "g") is set close to the time $\tau$ required for the acoustic oscillation pulse 5 to pass twice through the wall 3 of the container holding the liquid 6 being measured.

The maximum amplitude $U_5$ (FIG. 15b) of the pulse acoustic reverberation envelope 17 on the separated additional portion of the trailing edge thereof is expressed by the equation:

$$U_5 = U_{00} \alpha^{B_2 - 1} \cdot \left(1 - 2\frac{\Delta Z_1}{Z}\right)^{B_2}; \quad (102)$$

The amplitude $U_6$ of the pulse 55 (15h) corresponding to the additional portion of said envelope 17 is proportional to the maximum amplitude $U_5$ of said envelope 17 (FIG. 15b) on the additional portion:

$$U_6 = K_{13} U_5 = K_{13} U_{00} \alpha^{B_2 - 1} \cdot \left(1 - 2\frac{\Delta Z_1}{Z}\right)^{B_2}; \quad (103)$$

where $K_{13}$ is the proportionality factor.

Said pulse 55 is passed from the output of the second gating amplifier 54 (FIG. 10) to the input of the second peak detector 56 of the separated portion of said envelope 17, wherein it is converted into a direct current voltage with the amplitude $E_5$ (FIG. 15i) equal to the maximum amplitude $U_6$ of the pulse 55 (FIG. 15h). The obtained voltage is delivered to the emitter follower 57 (FIG. 10) producing a reference electric signal with the amplitude $E_4$ (FIG. 15f) proportional to the amplitude $U_6$ of the pulse 55 (FIG. 15h):

$$E_4 = K_{14} U_6 = K_{13} K_{14} U_{00} \alpha^{B_2 - 1} \left(1 - 2\frac{\Delta Z_1}{Z}\right)^{B_2}; \quad (104)$$

where $K_{14}$ is the proportionality factor.

The proportionality factors $K_{13}$ and $K_{14}$ are in this case set so that the difference $E_U$ between the reference electric signal (FIG. 15f) and the reference electric signal 20 (FIG. 15e) at the output of the measuring unit 23 (FIG. 10) is zero with the initial value $Z_{OI}$ of the acoustic impedance of the fluid 6 (that is with $Z_1 = 0$):

$$K_{13} K_{14} = K_{12} \alpha^{B_1 - B_2} \quad (105)$$

Thus, the reference electric signal (chart "f") is shaped with the amplitude $$E_4 = K_{12} U_{00} \alpha_1^{B-1} \cdot \left(1 - 2\frac{\Delta Z_1}{Z}\right)^{B_2}; \quad (106)$$

The difference signal $E_U$ delivered to the recorder 24 (FIG. 10) depends upon the variations $Z_1$ of the acoustic impedance of the fluid 6 as follows:

$$E_U = K_{12} U_{00} \alpha_1^{B-1} \left[\left(1 - 2\frac{\Delta Z_1}{Z}\right)^{B_2} - \left(1 - 2\frac{\Delta Z_1}{Z}\right)^{B_1}\right] \quad (107)$$

The sensitivity factor of the fluid property measurement is here expressed in the following way:

$$\beta_8 = \frac{1}{U_{004}} \frac{\delta E_U}{\delta\left(\frac{\Delta Z_1}{Z}\right)} = \quad (108)$$

$$2B_1 \frac{U_{00}}{U_{000}} \left[\left(1 - 2\frac{\Delta Z_1}{Z}\right)^{B_1-1} - \frac{B_2}{B_1}\left(1 - 2\frac{\Delta Z_1}{Z}\right)^{B_2-1}\right]$$

The above described embodiment of the device can be, due to elimination of the measurement zero drift, effectively used not only to monitor the boundary dividing two immiscible liquids and for discrete detection of the liquid level in containers, but for measuring the deviations of the fluid property from its initial value, for example, for measuring the concentration q of liquid solutions irrespective of the variations of $U_{oo}$. In this way the effect of variations in conditions of application of the acoustic oscillation pulse 5 to the container wall 3 and variations of the pulse amplitude upon the above mentioned types of measurement of the fluid properties is eliminated.

The neutralization of the effect of said variations in conditions of application of the pulse 5 to the container wall 3 and the amplitude thereof upon the sensitivity of the fluid property measurements, as well as elimination of the zero drift of the fluid property measurements, are achieved by dividing the voltages with respective amplitudes $E_3$ and $E_5$ (FIGS. 15e and 15i), generated from the pulses 48 and 55 (FIGS. 15d and 15h) and obtained by gating the main and additional, respectively, portions of the trailing edge of the pulse acoustic reverberation envelope 17.

Figure 10:
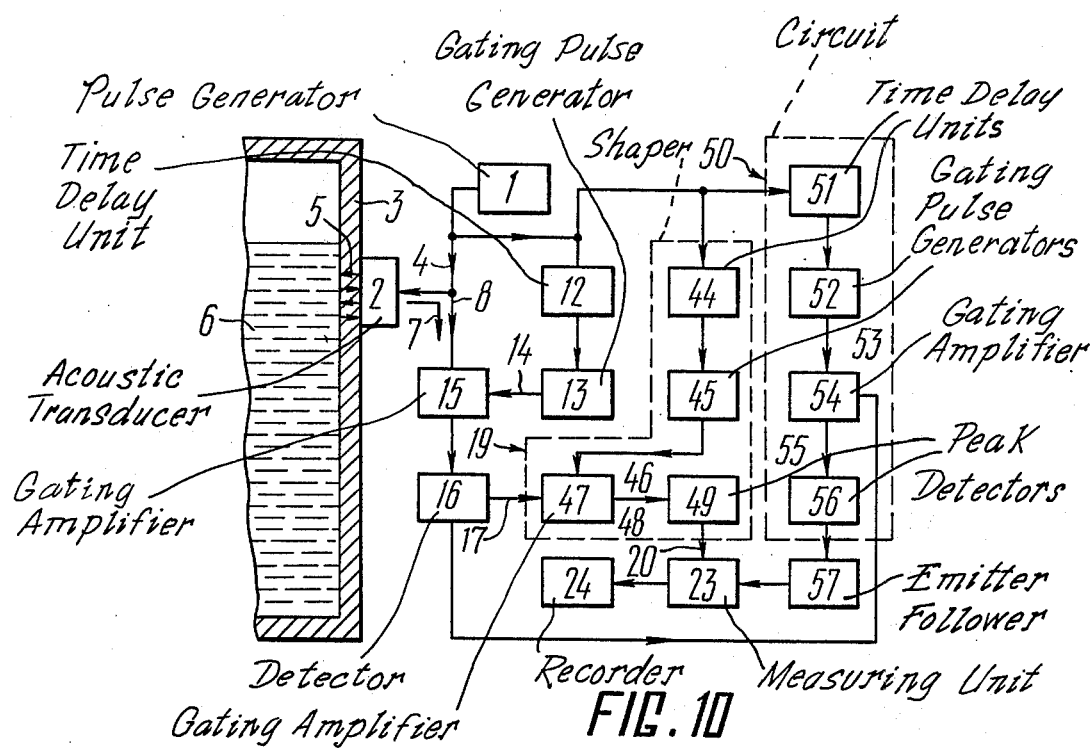
FIG. 10 is a block diagram showing the device of FIG. 9, featuring an additional electronic channel for separation of a second portion on the trailing edge of the pulse acoustic reverberation envelope, a peak detector of said portion and a differential measuring channel in the electrical circuit of the proposed device according to the invention.
Figure 11:
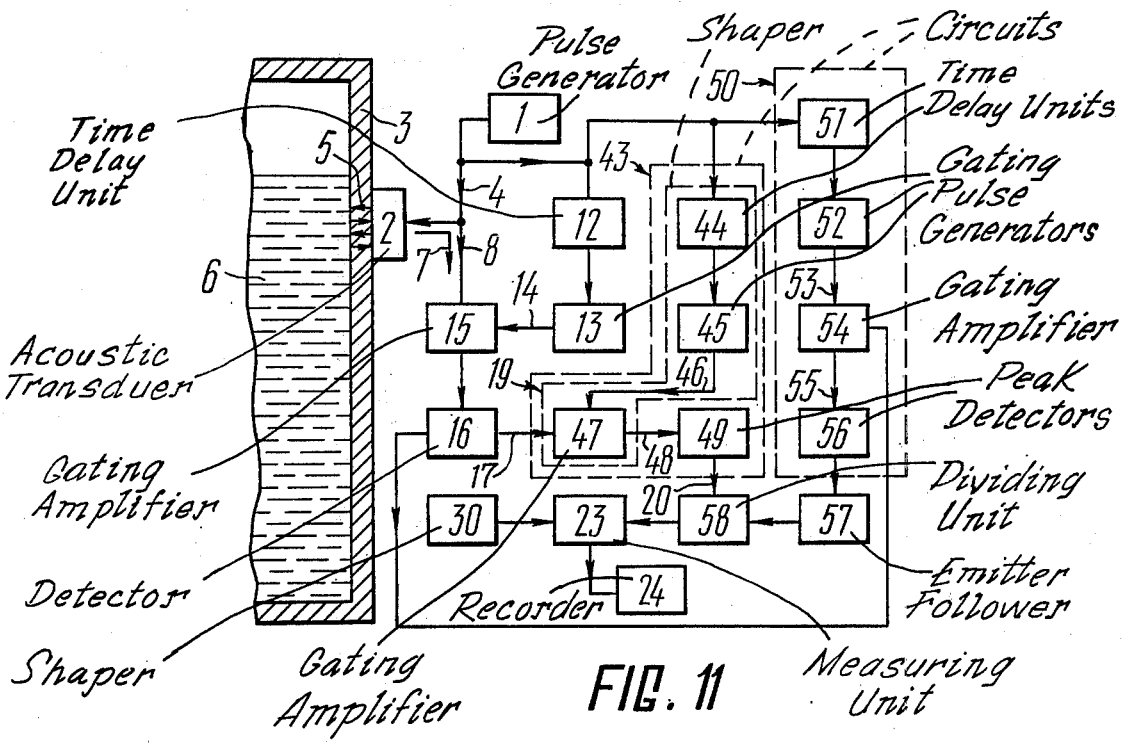
FIG. 11 is a block diagram showing the device of FIG. 9, featuring an additional electronic channel for separation of a second portion on the trailing edge of the pulse acoustic reverberation envelope, a peak detector of said channel, an electric signal dividing unit and a differential measuring channel in the electrical circuit of the proposed device, according to the invention.

In the embodiment of FIG. 11, where this object is achieved, separation of the pulse 55 corresponding to the additional portion of said envelope 17 and shaping an electric signal (voltage) with the amplitude $E_5$ (FIG. 15i) equal to the amplitude $U_6$ of the pulse 55 are performed by the circuit 50 (FIG. 11) similar to the previous embodiment of FIG. 10. This electric signal is passed from the output of the second peak detector 56 to one of the inputs of the electric signal dividing unit 58. The other input thereof is fed from the output of the peak detector 49 the data-carrying electric signal 20 (FIG. 15e). The electric signal with the amplitude $E_6$ equal to the quotient of the division of the electric signals delivered to the inputs of the unit 58 (FIG. 11) is formed at the output thereof:

$$E_6 = K_{14} U_{00} \cdot \frac{E_3}{E_5} = \frac{K_{12} \cdot K_{14} U_{000}}{K_{13}} \cdot \alpha_1^{B} \alpha_2^{-B} x \quad (109)$$

$$\times \left(1 - 2\frac{\Delta Z_1}{Z}\right)^{B_1 - B_2};$$

where $K_{14}$ is the proportionality factor.

The output electric signal of said dividing unit 58 is supplied to one of the inputs of the measuring unit 23 where it is compared to the reference electric signal with the amplitude $E_4$ (FIG. 15b) delivered from the reference electric signal shaper 30 (FIG. 11). In this case the amplitude $E_4$ of the reference electric signal is set equal to the amplitude of the output signal of the dividing unit 58, which corresponds to the initial value $Z_{OI}$ of the acoustic impedance of the fluid 6 (that is corresponds to $\Delta Z_1 = 0$):

$$E_4 = \frac{K_{12} K_{14}}{K_{13}} \alpha_1^{B} \alpha_2^{-B} \quad (110)$$

The difference signal $E_U = E_4 - E_6$ having an amplitude $$E_u = \frac{K_{12} K_{14}}{K_{13}} \alpha_1^{B} \alpha_2^{-B} \left[1 - \left(1 - 2\frac{\Delta Z_1}{Z}\right)^{B_1 - B_2}\right] \quad (111)$$

is supplied from the output of the measuring unit 23 to the recorder 24 whose scale is graduated in units of measurement of the fluid property of interest. The sensitivity factor $\beta g$ of measurements is in this case expressed as follows $$\beta_g = \frac{1}{U_{004}} \frac{\delta Eu}{\delta\left(\frac{\Delta Z_1}{Z}\right)} = 2 \frac{K_{14}}{K_{13}} (B_1 - B_2) \alpha_2^{1-B} \times \quad (112)$$

$$X\left(1 - 2\frac{\Delta Z_1}{Z}\right)^{B_1 - B_2 - 1}$$

For some fluids whose impedance is close to or more than the acoustic impedance of the container wall 3 the electric signal carrying information on the properties of the fluid 6 is shaped by finding the sign of the time interval between the leading edges of two hereropolar envelopes 17 and 18 of pulse acoustic reverberation.

Figure 12:
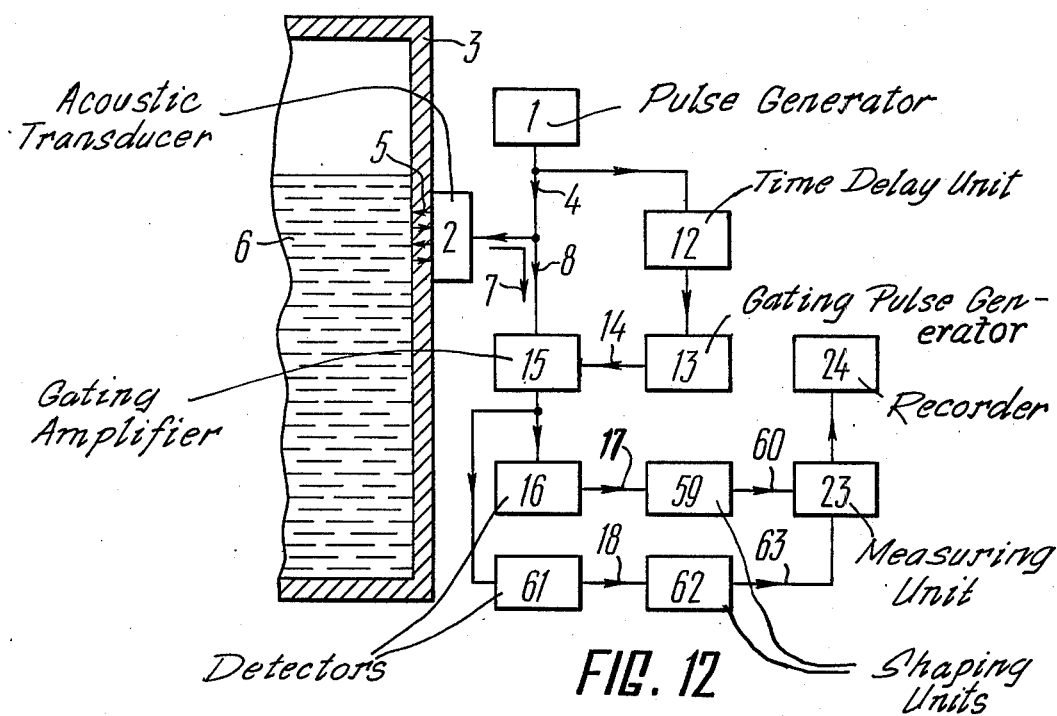
FIG. 12 is a block diagram showing the device of FIG. 1, featuring two units for shaping standard electric pulses from pulse acoustic reverberation envelopes and a unit for measuring the time difference between shaping of standard electric pulses in the electrical circuit of the proposed device, according to the invention.

In the embodiment of FIG. 12 this object is achieved as follows. The standard electric pulse shaping unit 59 produces the standard electric pulse 60 (FIG. 16e) corresponding to the leading edge of the pulse acoustic reverberation envelope 17. The second pulse acoustic reverberation envelope 18 is passed through the detector 61 (FIG. 12) to the second standard electric pulse shaping unit 62 which produces the standard electric pulse 63 (FIG. 16e) corresponding to the leading edge of the second pulse acoustic reverberation envelope 18 (chart "d").

The standard pulses 60 and 63 (FIGS. 16c and 16e) corresponding to the leading edges of the pulse acoustic reverberation envelopes 17 and 18 are supplied from the outputs of the shaping units 59 (FIG. 12) and 62 to the inputs of the measuring unit 23. The unit 23 produces in response to the pulses 60 and 63 fed to the inputs thereof a rectangular pulse (FIG. 16, chart "f") whose duration $\tau_{11}$ is equal to the time interval between the standard pulses 60 and 63 (charts "c" and "e"). The sign (positive or negative) of the output rectangular pulse of the measuring unit 23 (FIG. 12) depends on the ratio between the acoustic impedance $Z_1$ of the fluid 6 in the container and the acoustic impedance Z of the container wall 3. In case the ratio $Z_1/Z$ is less than one, this pulse (FIG. 16f) has a negative polarity.

In case the ratio $Z_1/Z$ is more than one, the shape and location of both envelopes 17' and 18' (FIGS. 16b and 16d) indicated by dotted lines) change. As a result the standard pulses are shifted in time and assume the position of the pulses 60' and 63' (FIGS. 16c and 16e) indicated by dotted lines). In response to the standard pulses 60' and 63' whose location was shifted in time the measuring unit 23 (FIG. 12) produces a rectangular pulse (FIG. 16 g) of a positive polarity.

The rectangular pulses (FIGS. 16f and 16g) whose sign carries information on the property of the fluid 6 (FIG. 12) are passed from the output of the measuring unit 23 to the recorder 24.

The above described method of measuring properties of a fluid in a container, realized in the devices of FIGS. 1, 3-12, ensures high efficiency contactless automatic measuring of various properties of fluids in containers in technological processes of many industries: metallurgy, ore cleaning, chemical, petrol, food industries and others.

What is claimed is:

1. A method of measuring properties of a fluid in a container, comprising the steps of: generating acoustic oscillation pulses; periodically applying said acoustic oscillation pulses to the fluid normally through the wall of the container holding the fluid receiving of heteropolar envelopes of pulse acoustic reverberations produced between the outer surface of the container and the fluid, said envelopes being used as acoustic signals, the reception of said pulse acoustic reverberation envelopes being in the zone of application of said acoustic oscillation pulses; and shaping an electric signal carrying information on the properties of the fluid from said received pulse acoustic reverberation envelopes.

2. A method as claimed in claim 1, wherein the step of shaping of the electric signal carrying information on the properties of said fluid is performed by determining the area limited by one of said pulse acoustic reverberation envelopes and the zero level thereof and determining the ratio of said area to the time interval proportional to the time interval between two successively applied said acoustic oscillation pulses.

3. A method as claimed in claim 2, further comprising the steps of: measuring the maximum amplitude of said envelope; comparing and maximum amplitude with said ratio of said area limited by said envelope and the zero level thereof to the time interval proportional to the time interval between two successively applied acoustic oscillation pulses.

4. A method as claimed in claim 1, wherein the step of shaping of the electric signal carrying information on the properties of said fluid is performed by separating portions on the leading and trailing edges of one of said pulse acoustic reverberation envelopes, whose respective ends lie on two amplitude levels at least one order of magnitude less than the maximum amplitude of said envelope and determining the time interval between said portions.

5. A method as claimed in claim 4, further comprising the steps of setting of the lower level of said two amplitude levels variable in proportion to the variations of the maximum amplitude of said pulse acoustic reverberation envelope.

6. A method as claimed in claim 1, wherein the step of shaping of the electric signal carrying information on the properties of said fluid is performed by separating a portion on the trailing edge of one of said pulse acoustic reverberation envelopes, whose respective ends lie on two amplitude levels at least one order of magnitude less than the maximum amplitude of said envelope, producing an electric pulse corresponding to said separated portion, producing a reference electric pulse at the instant corresponding to one of the positions of said produced electric pulse within the operating measuring range, and measuring the time interval between said produced electric pulse and said reference electric pulse.

7. A method as claimed in claim 6, wherein the step of said shaping of the reference electric pulse is performed with a time delay proportional to the variation of the maximum amplitude of said pulse acoustic reverberation envelope.

8. A method as claimed in claim 1, wherein the step of shaping of the electric signal carrying information on the properties of said fluid is performed by separating a portion on the trailing edge of one of said pulse acoustic reverberation envelopes, whose length is approximately equal to the double time required for said acoustic oscillation pulse to pass through the wall of the container and which is spaced from the leading edge of said envelope a distance divisible by at least double the time required for said acoustic oscillation pulse to pass through the wall of the container, and determining the maximum amplitude of said envelope at said separated portion.

9. A method as claimed in claim 8, further comprising the steps of separating a second portion of said pulse acoustic reverberation envelope between said first portion and the leading edge thereof, which is spaced from said first portion of said envelope to a distance divisible by double the time required for said acoustic oscillation pulse to pass through said wall of the container; and comparing the maximum amplitude of said envelope on said first and second portions.

10. A method as claimed in claim 1, wherein the step of shaping of the electric signal carrying information on the properties of said fluid is performed by determining the sign of the time interval between the leading edges of two said heteropolar envelopes of pulse acoustic reverberations.

11. A device for measuring properties of a fluid in a container, comprising: a pulse generator having an output; an acoustic transducer coupled to said output of said pulse generator and placed on the outer surface of the container wall, which produces acoustic oscillation pulses delivered to said fluid through said wall; an electric pulse time delay unit having an input and an output, said input of said time delay unit being coupled to said output of said pulse generator; a gating pulse generator having an input and an output, the input of said gating pulse generator being coupled to said output of said electric pulse time delay unit; a gating amplifier of acoustic signals having an input, a signal input and an output, said input of said gating amplifier being coupled to said output of said gating pulse generator, said signal input of said gating amplifier being coupled to said acoustic transducer, and said gating amplifier being arranged together with said electric pulse time delay unit and said gating pulse amplifier to receive by means of said acoustic transducer said acoustic oscillation pulses and to transform the same by means of said acoustic transducer into acoustic signals; a detector of the envelope of pulse acoustic reverberation produced between said outer surface of said wall of said container and said fluid, which ensures the use of said pulse acoustic reverberation envelope as said acoustic signal and has an input and an output, said input of said detector being coupled to said output of said gating amplifier; a shaper of a data-carrying signal carrying information on properties of said fluid, having a signal input, a controlled input and an output, said signal input of said shaper being electrically coupled to said output of said detector; a measuring unit having two inputs and an output, said first input of said measuring unit being electrically connected to said output of said data-carrying electric signal shaper; and a recorder having an input coupled to said output of said measuring unit.

12. A device as claimed in claim 11, wherein said data-carrying electric signal shaper comprises an integrator of said pulse acoustic reverberation envelope.

13. A device as claimed in claim 12, further comprising: a peak detector of said pulse acoustic reverberation envelope, having an input and an output, the input of said peak detector being coupled to said output of said detector of said pulse acoustic reverberation envelope and the output of said peak detector being electrically connected to said second input of said measuring unit, said measuring unit generally including a differential circuit.

14. A device as claimed in claim 12, further comprising: a peak detector of said pulse acoustic reverberation envelope, having an input connected to said otput of said detector of said pulse acoustic reverberation envelope and an output; an electric signal dividing unit having two inputs connected to respective said outputs of said peak detector of said pulse acoustic reverberation envelope and said integrator of said pulse acoustic reverberation envelope, and having an output coupled to said first input of said measuring unit; and a reference electric signal shaper having an output connected to said second input of said measuring unit, said measuring unit generally including a differential circuit.

15. A device as claimed in claim 11, further comprising: a unit for limiting said pulse acoustic reverberation envelope on two amplitude levels, which produces an electric pulse whose leading and trailing edges correspond to two separated portions of said pulse acoustic reverberation envelope, whose ends lie on said amplitude levels, and which has an input, a controlled input and an output, said input of said limiting unit being coupled to said output of said detector and the output of said limiting unit being coupled to said signal input of said data-carrying electric signal shaper; and an electric pulse duration measuring unit which is said data-carrying electric signal shaper.

16. A device as claimed in claim 15, further comprising: a peak detector of said pulse acoustic reverberation envelope for regulating the lower amplitude level of said separated portions of said pulse acoustic reverberation envelope, an input of said peak detector being coupled to said output of said detector of said pulse acoustic reverberation envelope, an output of said peak detector being electrically connected to said controlled input of said unit for limiting said pulse acoustic reverberation envelope on two amplitude levels.

17. A device as claimed in claim 11, further comprising: a unit for limiting said pulse acoustic reverberation envelope on two amplitude levels of said data-carrying electric signal shaper and for separating a portion on the trailing edge of said pulse acoustic reverberation envelope and having an input and an output, said input of said limiting unit serving as said signal input of said shaper; a differentiating unit of said data-carrying electric signal shaper for shaping an electric pulse corresponding to said separated portion of the trailing edge of said envelope, the input of said differentiating unit being coupled to said output of said limiting unit, the output of said differentiating unit serving as said output of said data-carrying electric signal shaper; an electric pulse time delay unit for shaping a reference electric signal and having an input, a controlled input and an output, said input of said time delay unit being coupled to said output of said pulse generator and said output of said time delay unit being coupled to said second input of said measuring unit; and a time interval measuring unit which serves as said measuring unit.

18. A device as claimed in claim 17, further comprising: a peak detector of said pulse acoustic reverberation envelope, having an input and an output, said input of said peak detector being coupled to said output of said detector of said pulse acoustic reverberation envelope; and an electric pulse time delay control unit having an input and an output, said input of said control unit being electrically connected to said output of said peak detector and said output of said control unit being coupled to said controlled input of said electric pulse time delay unit.

19. A device as claimed in claim 11, further comprising: a second time delay unit of electric pulses of said data-carrying electric signal shaper, having an input and an output, said input of said second time delay unit being coupled to said output of said pulse generator and serving as said controlled input of said data-carrying signal shaper; a second generator of gating pulses of said data-carrying electric signal shaper, having an input and an output, said input of said second gating pulse generator being coupled to said output of said second time delay unit; a gating amplifier of said pulse acoustic reverberation envelope of said data-carrying electrical signal shaper, having an input, a signal input and an output, said input of said gating amplifier of said pulse acoustic reverberation envelope being coupled to said output of the second gating pulse generating, and said signal input of said gating amplifier of said pulse acoustic reverberation envelope serving as said signal input of said data-carrying electric signal shaper, said gating amplifier of said pulse acoustic reverberation envelope being arranged together with said second time delay unit and second gating pulse generator to separate a portion on the trailing edge of said envelope; and a peak detector of said separated portion of said pulse acoustic reverberation envelope of said data-carrying electric signal shaper, having an input and an output, said input of said peak detector being coupled to said output of said gating amplifier of said pulse acoustic reverberation envelope, and said output of said peak detector serving as said output of said data-carrying electric signal shaper.

20. A device as claimed in claim 19, further comprising: a third electric pulse time delay unit having an input connected to said output of said pulse generator and an output; a third gating pulse generator having an input connected to said output of said third electrical pulse time delay unit and having an output; a second gating amplifier of the amplitude of said pulse acoustic reverberation envelope for separating a second portion on the trailing edge of said envelope, which is located between said first portion of said envelope and the leading edge thereof, and having an input, a signal input and an output, said input of said second gating amplifier, being connected to said output of said third gating pulse generator, said signal input of said second gating amplifier being connected to said output of said detector of said pulse acoustic reverberation envelope; and a second peak detector of said separated second portion of said pulse acoustic reverberation envelope, having an input connected to said output of said second gating amplifier and having an output, said output of said second peak detector being electrically connected to said second input of said measuring unit, said measuring unit generally including a differential circuit.

21. A device as claimed in claim 19, further comprising a third electric pulse time delay unit having an input connected to said output of said pulse generator and an output; a third gating pulse generator having an input connected to said output of said third electric pulse time delay unit and an output, a second gating amplifier of the amplitude of said pulse acoustic reverberation envelope for separating a second portion on the trailing edge of said envelope, which is located between said first portion of said envelope and its leading edge, and having an input, a signal input and an output, said input of said second gating amplifier being connected to said output of said third gating pulse generator, said signal input of said second gating amplifier being connected to said output of said detector of said pulse acoustic reverberation envelope; a second peak detector of said separated second portion of said pulse acoustic reverberation envelope, having an input connected to said output of said second gating amplifier and having an output; an electric signal dividing unit having two inputs electrically connected to respective said outputs of said first and second peak detectors and having an output, said output of said electric signal dividing unit being connected to said first input of said measuring unit; and a reference electric signal shaper having an output to said second input of said measuring unit, said measuring unit generally including a differential circuit.

22. A device as claimed in claim 11, further comprising: a standard electric pulse shaping unit which serves as said data-carrying electric signal shaper and ensures shaping of said standard electric pulse corresponding to the leading edge of said pulse acoustic reverberation envelope; a detector of the second pulse acoustic reverberation envelope, having an input and an output, said input of said detector of said second envelope being coupled to said output of said acoustic signal gating amplifier; a second standard electric pulse shaping unit designed to shape a standard electric pulse corresponding to the leading edge of said second pulse acoustic reverberation envelope and having an input and an output, said input of said second standard electric pulse shaping unit being coupled to said output of said detector of said second pulse acoustic reverberation envelope and said output of said second standard electric pulse shaping unit being coupled to said second input of said measuring unit; and a unit for measuring the time difference between shaping of said standard electric pulses corresponding to the leading edges of both said heteropolar envelopes of pulse acoustic reverberation, which serves as said measuring unit.

* * * * *